(12) United States Patent
Horton et al.

(10) Patent No.: US 9,713,519 B2
(45) Date of Patent: Jul. 25, 2017

(54) IMPLANTABLE PROSTHESIS

(71) Applicant: Atrium Medical Corporation, Hudson, NH (US)

(72) Inventors: Anthony R. Horton, Manchester, NH (US); Stephanie M. Santos, Arlington, MA (US)

(73) Assignee: Atrium Medical Corporation, Merrimack, NH (US)

( * ) Notice: Subject to any disclaimer, the term of this patent is extended or adjusted under 35 U.S.C. 154(b) by 446 days.

(21) Appl. No.: 13/734,554

(22) Filed: Jan. 4, 2013

(65) Prior Publication Data

US 2013/0178875 A1  Jul. 11, 2013

Related U.S. Application Data

(60) Provisional application No. 61/583,751, filed on Jan. 6, 2012.

(51) Int. Cl.
*A61F 2/00* (2006.01)
*A61L 31/02* (2006.01)
(Continued)

(52) U.S. Cl.
CPC .......... *A61F 2/0063* (2013.01); *A61L 31/022* (2013.01); *A61L 31/10* (2013.01);
(Continued)

(58) Field of Classification Search
CPC ...... A61F 2/0063; A61F 2/0077; A61F 2/105; A61F 2002/0068; A61F 2250/0084
(Continued)

(56) References Cited

U.S. PATENT DOCUMENTS

| 4,345,414 A | 8/1982 | Bornat et al. |
| 4,655,221 A * | 4/1987 | Devereux ............... 606/151 |

(Continued)

FOREIGN PATENT DOCUMENTS

| EP | 0655222 | 6/1998 |
| EP | 1219265 | 1/2003 |

(Continued)

OTHER PUBLICATIONS

International Search Report for International Application PCT/US2013/020340, dated Jun. 3, 2013.
(Continued)

*Primary Examiner* — Ryan J Severson
*Assistant Examiner* — Christian Knauss
(74) *Attorney, Agent, or Firm* — Wesley Scott Ashton

(57) ABSTRACT

An implantable prosthesis can have a three-dimensional shape that is invertible, so as to assume either a right configuration or a left configuration, which can be substantially mirror images of each other, so as to eliminate the need for separately manufacturing a left prosthesis and a right prosthesis. An implantable prosthesis can be preformed to independently assume a contoured three-dimensional shape that more adequately fits the extraperitoneal laparoscopic inguinal space, while simultaneously maintaining a relatively large area for fixation of the prostheses (e.g., through suturing or integration with the surrounding tissue). An implantable prosthesis can have a three-dimensional contoured shape that is formed from a single piece of continuous material, such as a mesh, and can possess substantially uniform rigidity. An implantable prosthesis may be trimmed, cut, or altered at an outer perimeter with no detrimental effect on its ability to independently maintain a predetermined three-dimensional contoured shape.

53 Claims, 13 Drawing Sheets

(51) Int. Cl.
*A61L 31/10* (2006.01)
*A61L 31/16* (2006.01)

(52) U.S. Cl.
CPC ....... *A61L 31/16* (2013.01); *A61F 2250/0084* (2013.01); *A61L 2300/252* (2013.01); *A61L 2300/416* (2013.01); *A61L 2300/606* (2013.01)

(58) Field of Classification Search
USPC .................... 606/151, 154; 623/23.72, 23.74
See application file for complete search history.

(56) References Cited

U.S. PATENT DOCUMENTS

| | | | |
|---|---|---|---|
| 4,769,038 | A | 9/1988 | Bendavid et al. |
| 5,356,432 | A * | 10/1994 | Rutkow et al. ............ 623/23.72 |
| 5,368,602 | A * | 11/1994 | de la Torre ................... 606/151 |
| 5,456,720 | A | 10/1995 | Schultz et al. |
| 5,468,242 | A * | 11/1995 | Reisberg ...................... 606/285 |
| 5,593,441 | A | 1/1997 | Lichtenstein et al. |
| 5,634,931 | A | 6/1997 | Kugel et al. |
| 5,827,325 | A | 10/1998 | Landgrebe et al. |
| 5,954,767 | A * | 9/1999 | Pajotin et al. ............. 623/23.72 |
| 6,066,777 | A | 5/2000 | Benchetrit |
| 6,120,539 | A | 9/2000 | Eldridge et al. |
| 6,258,124 | B1 | 7/2001 | Darois et al. |
| 6,287,316 | B1 * | 9/2001 | Agarwal ............... A61F 2/0063 606/151 |
| 6,368,541 | B1 | 4/2002 | Pajotin et al. |
| 6,596,002 | B2 * | 7/2003 | Therin et al. ................ 606/151 |
| 6,610,006 | B1 | 8/2003 | Amid et al. |
| 6,723,133 | B1 * | 4/2004 | Pajotin ....................... 623/23.72 |
| 6,740,122 | B1 | 5/2004 | Pajotin |
| 7,112,209 | B2 | 9/2006 | Ramshaw et al. |
| 8,298,290 | B2 | 10/2012 | Pélissier et al. |
| 2002/0013590 | A1 * | 1/2002 | Therin et al. ................ 606/151 |
| 2002/0077652 | A1 | 6/2002 | Kieturakis et al. |
| 2002/0103494 | A1 | 8/2002 | Pacey |
| 2003/0036803 | A1 | 2/2003 | McGhan et al. |
| 2003/0181988 | A1 * | 9/2003 | Rousseau ................... 623/23.72 |
| 2003/0187516 | A1 | 10/2003 | Amid et al. |
| 2003/0212462 | A1 * | 11/2003 | Gryska et al. ............. 623/23.72 |
| 2004/0092969 | A1 * | 5/2004 | Kumar .......................... 606/151 |
| 2006/0064175 | A1 * | 3/2006 | Pelissier et al. .......... 623/23.72 |
| 2007/0276487 | A1 * | 11/2007 | Carteron et al. ........... 623/11.11 |
| 2008/0071385 | A1 * | 3/2008 | Binette et al. ............. 623/23.72 |
| 2009/0082864 | A1 * | 3/2009 | Chen ......................... A61F 2/12 623/8 |
| 2009/0208552 | A1 * | 8/2009 | Faucher ............. A61K 31/4353 424/423 |
| 2009/0240288 | A1 * | 9/2009 | Guetty ................. A61F 2/0063 606/285 |
| 2009/0259235 | A1 * | 10/2009 | Doucet et al. ................ 606/151 |
| 2009/0270999 | A1 * | 10/2009 | Brown ....................... 623/23.72 |
| 2010/0318108 | A1 * | 12/2010 | Datta et al. ................... 601/151 |
| 2011/0144667 | A1 * | 6/2011 | Horton et al. ................ 606/151 |
| 2012/0259348 | A1 * | 10/2012 | Paul ............................ 606/151 |

FOREIGN PATENT DOCUMENTS

| | | |
|---|---|---|
| WO | WO 96-41588 | 12/1996 |
| WO | WO 99/56664 | 11/1999 |
| WO | WO 01-85060 | 11/2001 |
| WO | WO 02/22047 | 3/2002 |
| WO | WO 03/073960 | 2/2003 |
| WO | WO 03/094787 | 11/2003 |
| WO | WO 03/105727 | 12/2003 |
| WO | WO 2006-032812 | 6/2006 |

OTHER PUBLICATIONS

Bard FDA 510K Approval (Jan. 2001).
Bard Internet Publication (Apr. 2001).
Bard FDA 510K Approval (Jul. 2002).
Bellon, et al., "Evaluation of a New Composite Prosthesis (PL-PU99) for the Repair of Abdominal Wall Defects in Terms of Behavior at the Peritoneal Interface," *World Journal of Surgery*, 26: 661-666 (2002).
Bendavid, et al., "A Femoral 'Umbrella' for Femoral Hernial Repair Surgery," *Gynecology and Obstetrics*, 165: 153-156 (1987).
Bendavid, et al., New Techniques in Hernia Repair, *World Journal of Surgery*, 13: 522-531 (1989).
Greenawalt, et al., "Evaluation of Sepramesh Biosurgical Composite in a Rabbit Hernia Repair Model," *Journal of Surgical Research*, 94: 92-98 (2000).
Helfrich, et al., "Abdominal Wall Hernia Repair: Use of the Gianturco-Helfrich-Eberbach Hernia Mesh," *Journal of Laparoendoscopic Surgery*, 5(2): 91-96 (1995).
Kugel, et al., "Minimally Invasive, Nonlaparoscopic, Preperitoneal, and Sutureless, Inguinal Herniorraphy," *The American Journal of Surgery*, 178: 298-302 (1999).
Lichtenstein, et al., "Repair of Recurrent Ventral Hernias by an Internal 'Binder'", *The American Journal of Surgery*, 132: 121-125 (1976).
Moreno-Egea, "Laparoscopic repair of Ventral and Incisional Hernias Using a new Composite Mesh (Parietex)," *Surgical Laparoscopy, Endoscopy & Percutaneous Techniques*, 11(2): 103-106 (2001).
"Sharper Curve, Stronger Egg", Inside Science, printed Jan. 21, 2016, http://www.insidescience.org/content/sharper-curve-stronger-egg/779, 6 pages.

* cited by examiner

IMPLANTABLE PROSTHESIS

RELATED APPLICATION

This application claims priority to, and the benefit of, U.S. Provisional Application No. 61/583,751, filed Jan. 6, 2012, for all subject matter common to both applications. The disclosure of said provisional application is hereby incorporated by reference in its entirety.

FIELD OF THE INVENTION

The present invention relates to implantable prostheses suitable for treating an existing defect, or preventing a future defect, such as tissue or muscle wall defects. More particularly, the present invention relates to prostheses for treating inguinal hernias and other medical conditions requiring prosthetic reinforcement.

BACKGROUND OF THE INVENTION

A hernia is a protrusion of a tissue, structure, or part of an organ through the muscle tissue or the membrane by which it is normally contained. Inguinal hernias are one common type of hernia. In an inguinal hernia, a weakness in the abdominal wall grows into a hole, or defect. Tissue may protrude from the defect. Example hernias include umbilical hernias, in which intra-abdominal contents protrude through a weakness at the site of passage of the umbilical cord through the abdominal wall, and incisional hernias, which occur in an area of weakness caused by an incompletely-healed surgical wound. Those of skill in the art will appreciate that there are other types of hernias in addition to those specifically mentioned herein.

In order to treat a hernia, such as an inguinal hernia, a doctor may insert a specially designed patch or implantable prosthesis into an incision near the defect, e.g., near the naval. One example of such a medical procedure for implanting a prosthesis is totally extraperitoneal laparoscopic surgery. Implantable prostheses for repairing anatomical defects in tissue or muscle walls typically are designed to be larger than the defect so as to ensure adequate coverage and/or sufficient fixation of the prosthesis. During implantation, the prosthesis is folded and/or pushed through the incision. In order to allow the prosthesis to be positioned, it may include positioning straps, portions designed for suturing to the surrounding environment, and/or portions designed for fixation via in-growth of surrounding cells into the prosthesis. Once implanted, the prosthesis unfolds and is maneuvered into a suitable position. The positioned prosthesis is then secured by fixation. For example, fixation can include suturing the positioning straps to the margins of the defect, suturing a part of the body of the patch to the connective tissue, and allowing natural in-growth to occur. Excess material, such as excess material on the positioning strap, can be removed and the incision can be closed.

Some existing prostheses are manufactured to possess a flat, two dimensional shape. Such a shape is unsuitable for meeting the needs of repairing defects in some tissue or muscle walls. In particular, inguinal hernia repairs place stringent demands upon suitable shapes for implantable prostheses since the laparoscopic inguinal region is extremely complicated and includes many blood vessels, nerves, ligaments, and other anatomical components. Accordingly, the space in which the prosthesis is deployed contains many bumps, irregularities, and contours, which may be symmetrical or asymmetrical. Using flat, two dimensional prostheses thus places the burden of fitting the prosthesis to the anatomical region upon the surgeon. This results in additional required training for surgeons performing such operations. Furthermore, processes involving flat two dimensional prostheses generally are associated with a high learning curve, given the complexity of many anatomical regions, including the inguinal region. One of skill in the art can appreciate that such extended training and additional expertise generally increases the associated costs of such procedures, which is undesirable for patients and other consumers.

Existing attempts to solve the problem of providing a prosthesis that adequately accommodates the shape of a given anatomical region have included constructing preformed prostheses that independently assume a predetermined three-dimensional shape. Such preformed three-dimensional prostheses generally are much more effective at assuming the shape of an anatomical region, which thus reduces the required training, the length of the surgical procedure, and risk of error by the surgeon. Additionally, preformed three-dimensional prostheses can be associated with the benefit of not requiring suturing to ligaments or connective tissue, for example by using medical tacks. Rather, they can adequately enable in-growth fixation methods, which tend to reduce pain and/or discomfort in the patient, lower patient recovery time, shorten patient discharge time from the hospital, etc.

However, some existing preformed three-dimensional prostheses require additional support, such as for example, a rigidified peripheral edge at the perimeter of the body to independently maintain the predetermined three-dimensional shape. The rigidified peripheral edge can be formed, for example, by ultrasonic welding, making the perimeter substantially more rigid or rigidified relative to the remaining portions of the mesh prosthesis. The increased rigidity of the peripheral edge permits some degree of flexibility (e.g., to enable rolling) while also promoting the prosthesis' ability to assume the shape outlined by the rigidified peripheral edge. Prior designs require this rigidified peripheral edge to satisfy the intended function of independently assuming and reassuming a predetermined three-dimensional shape.

For prostheses having rigidified edges, trimming, cutting, removing, or otherwise altering portions of the rigidified peripheral edge or even the body itself are prohibited because to interrupt, break, or remove portions of the rigidified peripheral edge or perimeter significantly impacts the prosthesis' ability to independently assume the intended predetermined shape. The result is the undesirable consequence of the prosthesis losing its desired preformed three-dimensional contoured shape, and therefore becoming much more difficult to handle and position. In other words, for those prostheses that rely on the more rigid peripheral edge to maintain their shape, removal or interruption of portions of that edge dramatically affect the adaptability of such prostheses to a variety of different circumstances, anatomies, and/or procedures.

An additional shortcoming of existing prostheses is that, given the unique and asymmetrical shape of the internal region in the human body, known prostheses must be manufactured and sold as either a right prosthesis (oriented for the right side of the human body) or a left prosthesis (oriented for the left side of the human body). Accordingly, additional templates, molds, and other manufacturing machinery are required in order to build and sell both left orientation prostheses and right orientation prostheses. This requirement for duplicate manufacturing equipment places an additional financial burden on manufacturers. Furthermore, the requirement for both left and right prostheses requires hospitals to maintain a sufficient stock of both left prostheses and right prostheses, thereby increases inventory costs. In many cases, such added costs are simply passed on to the patient, resulting in a higher economic barrier for laparoscopic surgery, thus making such treatment methods less accessible or affordable to the general public.

SUMMARY

There is a need for an implantable prosthesis that better fits the shape of the extraperitoneal laparoscopic inguinal anatomical region and surrounding region of the defect being treated, and which can more easily be maintained in the desired implanted location. Additionally, there is a need for a three-dimensional implantable prosthesis having greater ability to be customized according to specific patient body types, proportions, and intended repair sites, without losing its remaining shape and effectiveness after customization. Finally, there remains a need for an implantable prosthesis capable of being made through an enhanced, more economical manufacturing process. The present invention is directed toward further solutions to address this need, in addition to having other desirable characteristics.

In accordance with one embodiment of the present invention, an implantable prosthesis for repairing a defect in a muscle or tissue wall can include a preformed flexible body having a three-dimensional contoured shape. The preformed flexible body can include a first end, a second end opposite the first end, and a perimeter incorporating the first end and the second end. The body can independently assume the contoured shape. The contoured shape can include an open sided bowl at the first end of the body, a substantially planar area at the second end of the body, and a transitional area coupling the open sided bowl of the first end with the substantially planar area of the second end. The transitional area can include an arch region coupled with a curved and banked region. Following along the perimeter, the arch region can lead to the open sided bowl which can lead to the curved and banked region which can lead to the substantially planar area which can lead to the arch region, thereby completing the perimeter. To be clear, the perimeter is substantially the same construct as the material of the body leading up to the perimeter or edge, such that a clinical user can trim or shape the perimeter and result in the same perimeter or edge rigidity construct.

In accordance with further aspects of the present invention, the body can be constructed from a single, continuous piece of material. The body can maintain a shape memory. Additionally or alternatively, the body can be configured in such a way as to deform under at least a minimum predetermined force typically experienced during implantation against the muscle or tissue wall. Furthermore, the body also can be configured to re-assume the contoured shape upon a release of the force. The substantially planar area can be shaped and dimensioned to be affixed to a portion of a pelvic wall. The arch region can be shaped and dimensioned to accommodate one or more external iliac vessels. The open sided bowl can be shaped and dimensioned to substantially replicate the shape of a lateral TEP space. The curved and banked region can be shaped and dimensioned to substantially replicate a shape of an abdominal wall. The body of the prosthesis can be sized and dimensioned to cover a large direct hernia defect while being affixed to a Cooper's ligament. The body can exclude a perimeter that is rigidified relative to a remainder of the body. A rigidity of the body can be substantially uniform, e.g., across substantially all of the body. If an outer portion of the body is trimmed off, then the shape of the remaining three-dimensional contoured portion of the body can be substantially unaffected or substantially not changed. The preformed body can include a coated mesh that is preformed, and the coated mesh can include, as coating, a non-polymeric bioabsorbable cross-linked fatty acid based material, the cross-links formed of ester bonds, lactone bonds, or both. The preformed body further can include a coating derived from fish oil. The preformed body further can include a coating derived from an omega-3 fatty acid. The preformed body further can include a coating derived from eicosapentaenoic (EPA) and docosahexaenoic (DHA) fatty acids. The body further can include a mesh having strands forming intersections, wherein a coating is at least partially disposed within the intersections. The body can be invertible between a left orientation and a right orientation, the left orientation and the right orientation can be substantially mirror images of each other. When the body is comprised of a mesh having strands forming a plurality of intersections, the three-dimensional contoured shape can be maintained by interaction of the plurality of intersections with each other imparting structure to form and maintain the three-dimensional contoured shape configuration.

In accordance with one embodiment of the present invention, an implantable prosthesis for repairing a defect in a muscle or tissue wall can include a preformed body configured to independently assume a predetermined three-dimensional contoured shape. The body can include a single, continuous piece of mesh having strands forming intersections, a coating disposed at least partially within the intersections of the strands of the mesh, an inner portion and a perimeter surrounding the inner portion. The inner portion and the perimeter can be about equally rigid, such that the inner portion is able to independently assume a subset of the predetermined three-dimensional contoured shape if the perimeter is removed or modified.

In accordance with further aspects of the present invention, the three-dimensional contoured shape can include an open sided bowl at a first end of the body, a substantially planar area at a second end of the body opposite the first end, and a transitional area coupling the open sided bowl of the first end with the substantially planar area of the second end. The transitional area can include an arch region coupled with a curved and banked region. Following along the perimeter, the arch region can lead to the open sided bowl which can lead to the curved and banked region which can lead to the substantially planar area which can lead to the arch region, thereby completing the perimeter. The body can be constructed from a single, continuous piece of material. The body can maintain a shape memory. Additionally or alternatively, the body can be configured in such a way as to deform under at least a minimum predetermined force typically experienced during implantation against the muscle or tissue wall and further can be configured re-assume the contoured shape upon a release of the force. The substantially planar area can be shaped and dimensioned to be affixed to a portion of a pelvic wall. The arch region can be shaped and dimensioned to accommodate one or more external iliac vessels. The open sided bowl can be shaped and dimensioned to substantially replicate the shape of a lateral TEP space. The curved and banked region can be shaped and dimensioned to substantially replicate a shape of an abdominal wall. The body of the prosthesis can be sized and dimensioned to cover a large direct hernia defect while being affixed to a Cooper's ligament. The body can exclude a perimeter that is rigidified relative to a remainder of the body. The rigidity of the inner portion can be substantially uniform, and the rigidity of the perimeter can be substantially uniform. In this manner, the inner portion and the perimeter both can have the same substantially uniform rigidity. If an outer portion of the body is trimmed off, then the shape of the remaining portion of the three-dimensional contoured body can be substantially unaffected or not changed. The preformed body can include a coated mesh that is preformed, and the coated mesh can include a non-polymeric bioabsorbable cross-linked fatty acid based material, the cross-links formed of ester bonds, lactone bonds, or both. The preformed body further can include a coating derived from fish oil. The preformed body further can include a coating derived from an omega-3 fatty acid. The preformed body further can include a coating derived from eicosapentaenoic (EPA) and docosahexaenoic (DHA) fatty acids. The preformed body further can include a mesh having strands forming intersections, and a coating can be at least partially disposed within the intersections. The body can be invertible between a left orientation and a right orientation, and the left orientation and the right orientation can be substantially mirror images of each other. When the body is comprised of a mesh having strands forming a plurality of intersections, the three-dimensional contoured shape can be maintained by interaction of the plurality of intersections with each other imparting structure to form and maintain the three-dimensional contoured shape configuration.

In accordance with one embodiment of the present invention, an implantable prosthesis for repairing a defect in a muscle or tissue wall can include a preformed flexible body. The preformed flexible body can include a single, continuous piece of mesh, and the preformed body can be configured to independently assume a predetermined three-dimensional contoured shape. The shape can include a substantially planar area and one or more non-uniform curvatures deviating away from the planar area. The body can be invertible between a left orientation and a right orientation, and the left orientation and the right orientation can be substantially mirror images of each other.

In accordance with further aspects of the present invention, the shape of the body can include an open sided bowl at a first end of the body, a substantially planar area at a second end of the body opposite the first end; and a transitional area coupling the open sided bowl of the first end with the substantially planar area of the second end. The transitional area can include an arch region coupled with a curved and banked region. Following along a perimeter, the arch region can lead to the open sided bowl which can lead to the curved and banked region which can lead to the substantially planar area which can lead to the arch region, thereby completing the perimeter. The body can be constructed from a single, continuous piece of material. The body can maintain a shape memory and thus can be configured in such a way as to deform under at least a minimum predetermined force typically experienced during implantation against the muscle or tissue wall and further can be configured to re-assume the contoured shape upon a release of the force. The substantially planar area can be shaped and dimensioned to be affixed to a portion of a pelvic wall. The arch region can be shaped and dimensioned to accommodate one or more external iliac vessels. The open sided bowl can be shaped and dimensioned to substantially replicate the shape of a lateral TEP space. The curved and banked region can be shaped and dimensioned to substantially replicate a shape of an abdominal wall. The body of the prosthesis can be sized and dimensioned to cover a large direct hernia defect while being affixed to a Cooper's ligament. The body can exclude a perimeter or peripheral portion that is rigidified relative to a remainder of the body. The shape can include an outer portion extending along an entire perimeter and a remaining inner portion enclosed within the outer portion. The rigidity of the inner portion can be substantially uniform and the rigidity of the outer portion can be substantially uniform. The rigidity of the outer portion can be substantially equal to the rigidity of the inner portion, such that the inner portion and the outer portion have substantially the same substantially uniform rigidity. If an outer portion of the body is trimmed off, then the shape of the remaining portion of the three-dimensional contoured body can be substantially unaffected or not changed. The preformed body can include a coated mesh that is preformed, and the coated mesh can include (as a coating) a non-polymeric bioabsorbable cross-linked fatty acid based material, the cross-links formed of ester bonds, lactone bonds, or both. The preformed body further can include a coating derived from fish oil. The preformed body further can include a coating derived from an omega-3 fatty acid. The preformed body further can include a coating derived from eicosapentaenoic (EPA) and docosahexaenoic (DHA) fatty acids. The body further can include a mesh having strands forming intersections, and a coating can be at least partially disposed within the intersections. When the body is comprised of a mesh having strands forming a plurality of intersections, the three-dimensional contoured shape can be maintained by interaction of the plurality of intersections with each other imparting structure to form and maintain the three-dimensional contoured shape configuration.

In accordance with one embodiment of the present invention, a method for fabricating an implantable prosthesis for repairing a defect in a muscle or tissue wall can include providing a coating to a single piece of mesh that includes strands forming a plurality of intersections, such that the coating is disposed at least partially within the intersections of the mesh. The coating on the mesh can be cured at one or more predetermined temperatures for one or more predetermined times. A template can be provided having a predetermined shape. The mesh can be placed in the template. The mesh can be heated in the template at one or more predetermined temperatures for one or more predetermined times so that the mesh retains the predetermined shape, thereby forming the implantable prosthesis. The implantable prosthesis can be removed from the template.

In accordance with further aspects of the present invention, the coating can be provided by dipping, brushing, pumping, direct deposit via a conduit connected to a fluid reservoir. The mesh can be heated at a temperature of about 130° C. to about 800° C. for a period of about 0.1 minutes to about 20 minutes. The coating on the mesh can be cured at a temperature of about 50° C. to about 121° C. for a period of about 8 hours to about 48 hours. The mesh can be cooled subsequent to heating the mesh. The mesh can be cooled at a temperature of about 0° C. to about 23° C. for a period of about 1 minute to about 20 minutes. The mesh can be subjected to a force applied by a press while the mesh is being heated in the template.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1A:
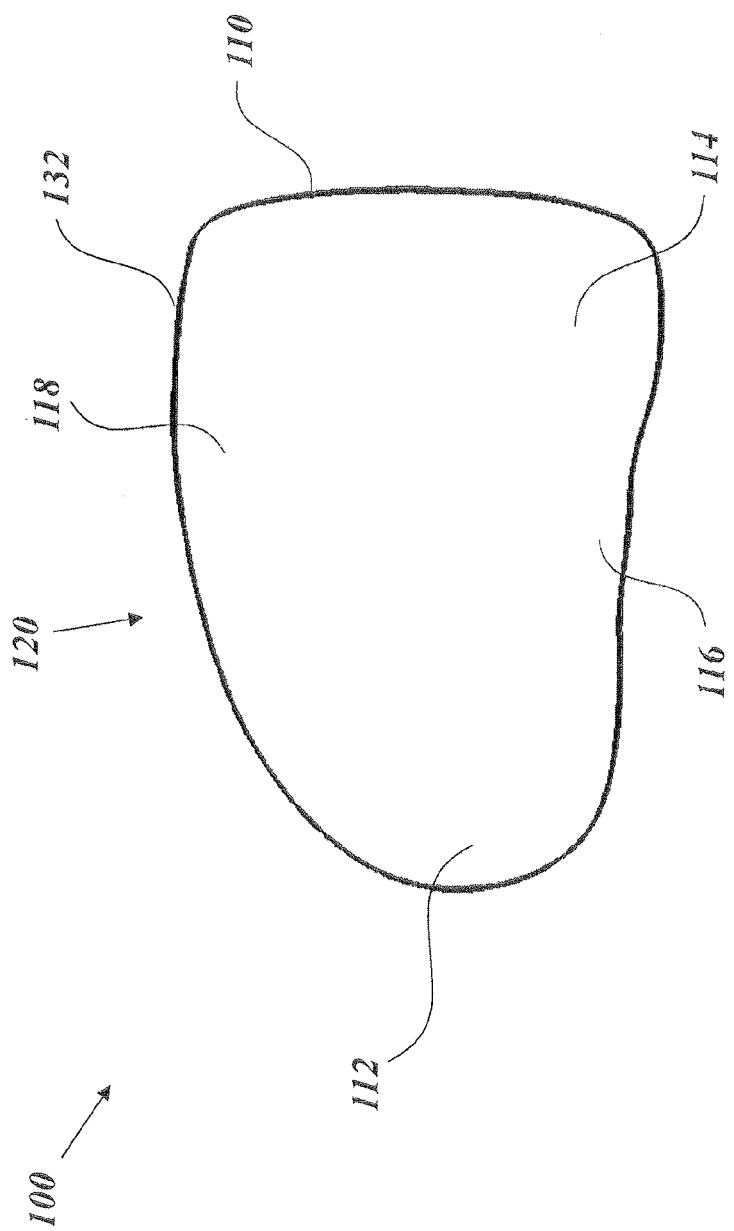
FIG. 1A is a top view of a three-dimensional shaped prosthesis, according to embodiments of the present invention.

Illustrative embodiments of the present invention provide implantable prostheses possessing several key improvements over existing art. In particular, prostheses according to the present invention can have a three-dimensional contoured shape that is formed from a single piece of flexible continuous material such as a mesh, and can possess substantially uniform values of rigidity and/or flexibility. Such prostheses may be trimmed or cut at an outer perimeter prior to implantation with no detrimental effect on its ability to independently maintain a predetermined three-dimensional contoured shape or a subset of such a predetermined shape. Said differently, the removal of a portion of the perimeter by trimming or other method to customize the outer profile shape of the prosthesis does not affect the ability of the prosthesis to maintain its three-dimensional contoured shape. The three-dimensional contoured shape does not rely on any form of rigidified or other structure along a periphery having a different rigidity or flexibility from the main body of the prosthesis in order to maintain the three-dimensional contoured shape. Said differently, there is no rigidified perimeter imparting structure to form the contoured shape. Furthermore, prostheses according to the present invention can be preformed to have a three-dimensional shape that more adequately fits the extraperitoneal laparoscopic inguinal space, while simultaneously maintaining a relatively large area for fixation of the prostheses (e.g., through suturing or in-growth integration with the surrounding tissue). In addition, prostheses according to the present invention can have a three-dimensional shape that is invertible, so as to assume either a right orientation or a left orientation, which can be substantially mirror images of each other. Such prostheses can be conveniently switched between the right orientation and the left orientation, so as to eliminate the need for separately manufacturing a left prosthesis and a right prosthesis with separate and distinct forms.

FIGS. 1A through 9, wherein like parts are designated by like reference numerals throughout, illustrate example embodiments of implantable prostheses that is invertible to select a left or right orientation, according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of materials, in a manner still in keeping with the spirit and scope of the present invention.

Figure 2:
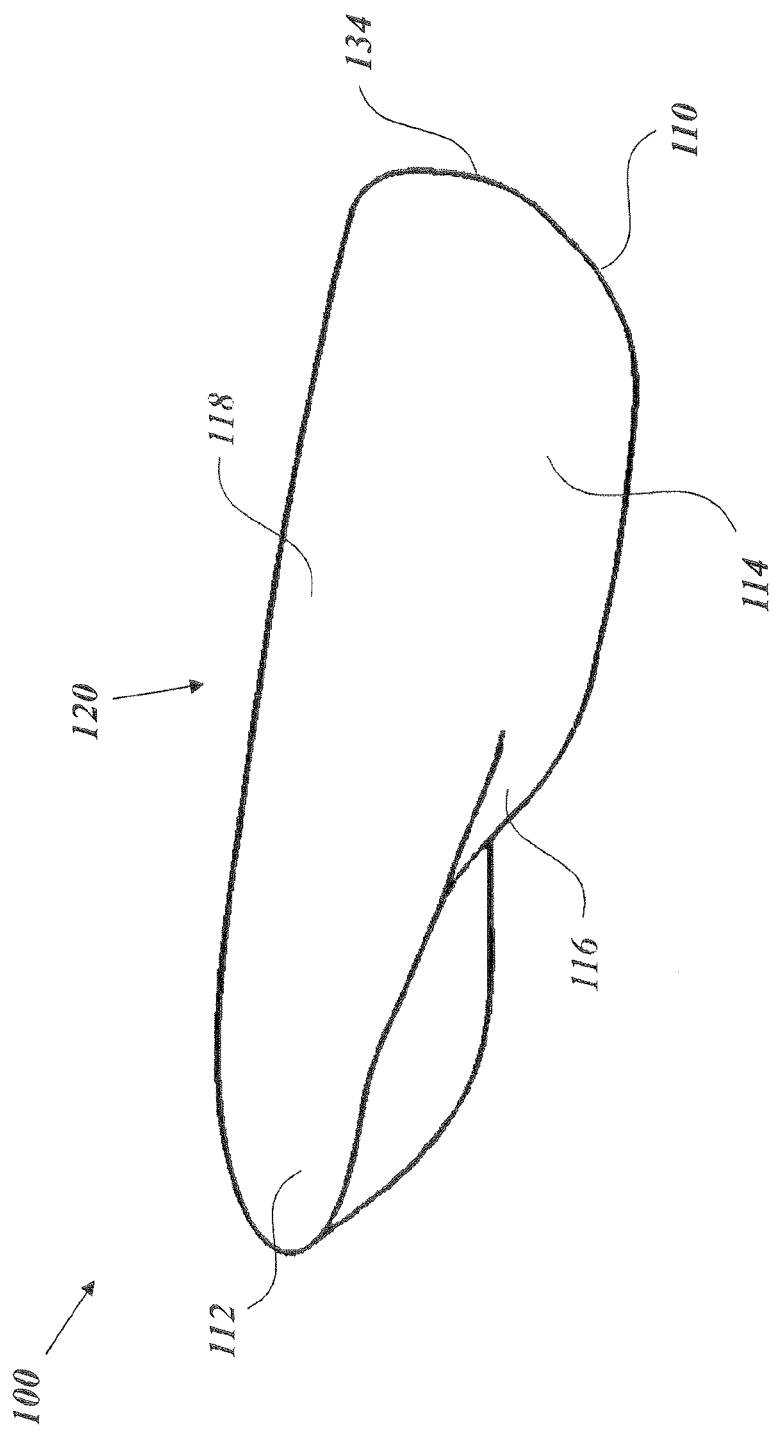
FIG. 2 is an isometric view of the three-dimensional shaped prosthesis of FIG. 1, according to aspects of the present invention.
Figure 3A:
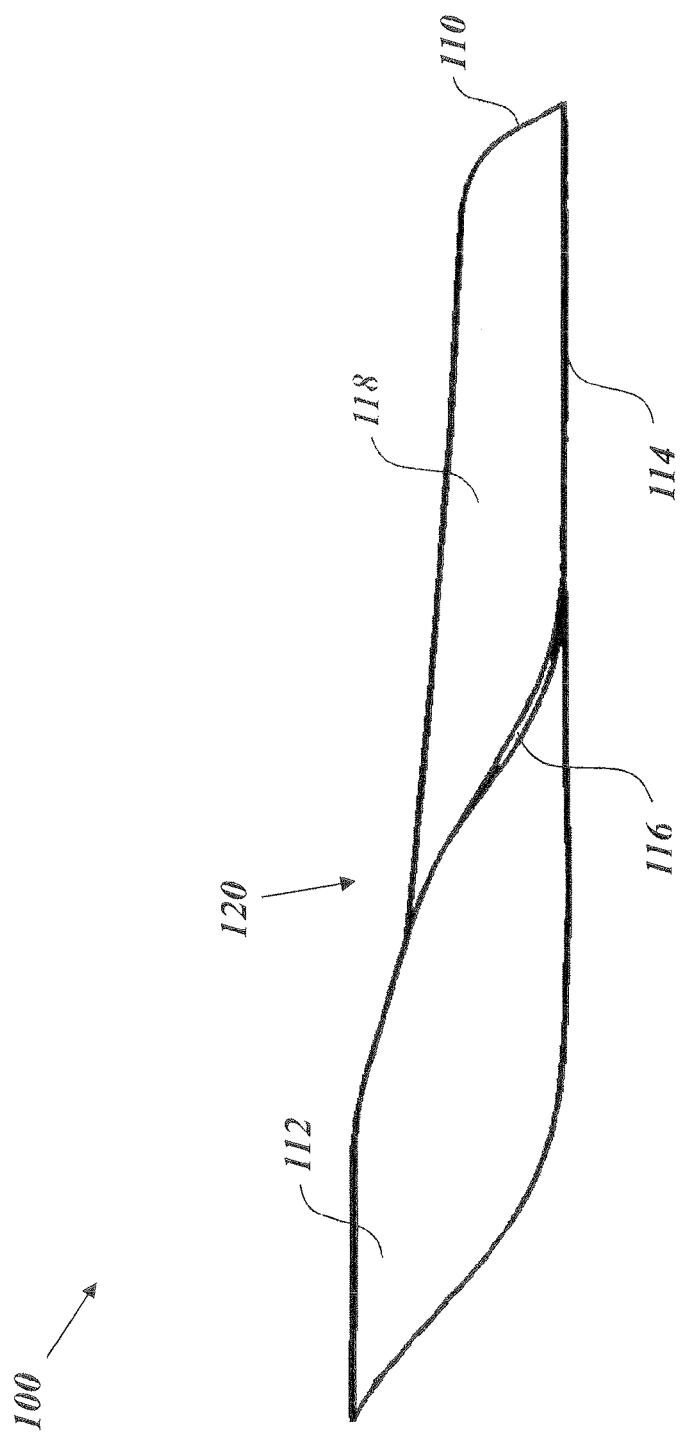
FIG. 3A is a side view of the three-dimensional shaped prosthesis of FIG. 1, according to aspects of the present invention.

FIGS. 1A, 2, and 3A depict a top view, an isometric view, and a side view, respectively, of a prosthesis according to an embodiment of the present invention. The prosthesis includes a body 100 and a perimeter 110. The body 100 forms a three-dimensional shape having a substantially planar area 114 and one or more curvatures deviating away from the substantially planar area 114. The curvatures can include an open sided bowl 112, an arch region 116, and a curved and banked region 118. The open sided bowl 112 and the substantially planar area 114 are situated at opposite ends, such that the open sided bowl 112 is at a first end of the body 100 and the substantially planar area is at a second end of the body 100 that is opposite the first end. Likewise, in accordance with one example embodiment of the present invention, the arch region 116 and the curved banked region 118 are on substantially opposite sides of the body 100, as is illustrated in the corresponding figures.

Figure 3B:
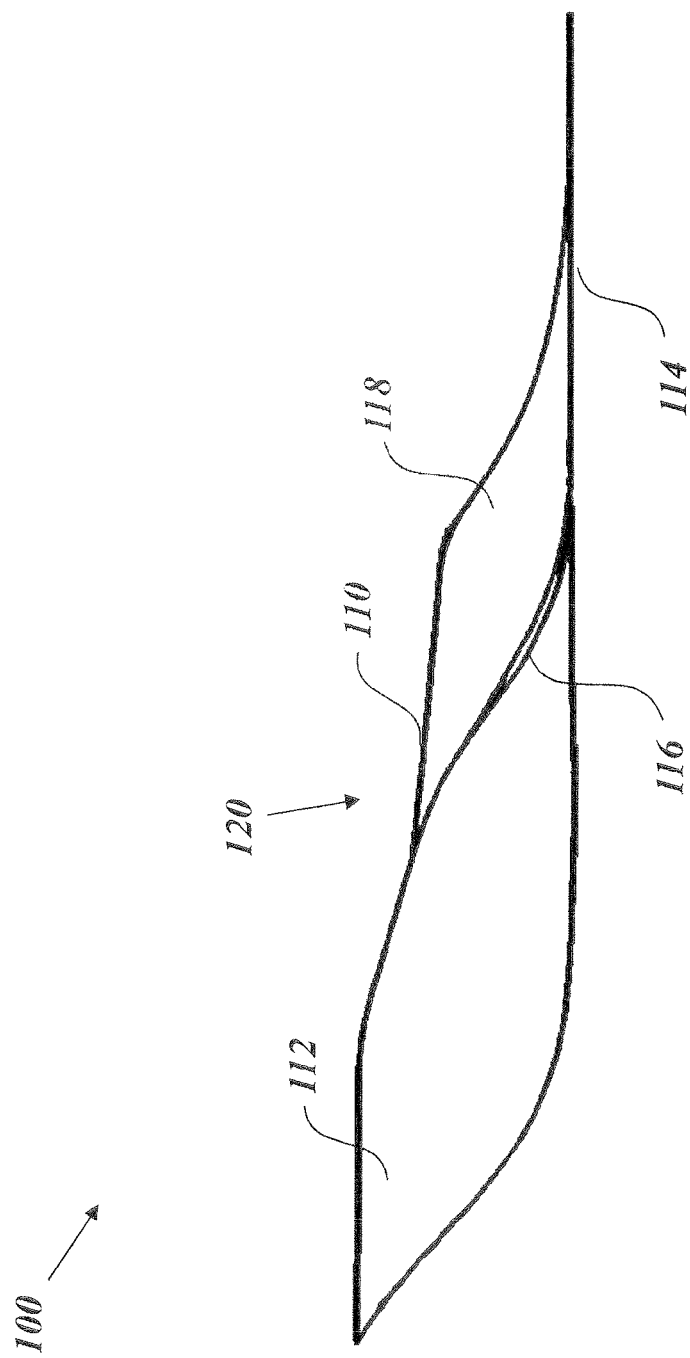
FIG. 3B is a side view of an embodiment of a three-dimensional shaped prosthesis, according to the present invention.
Figure 4:
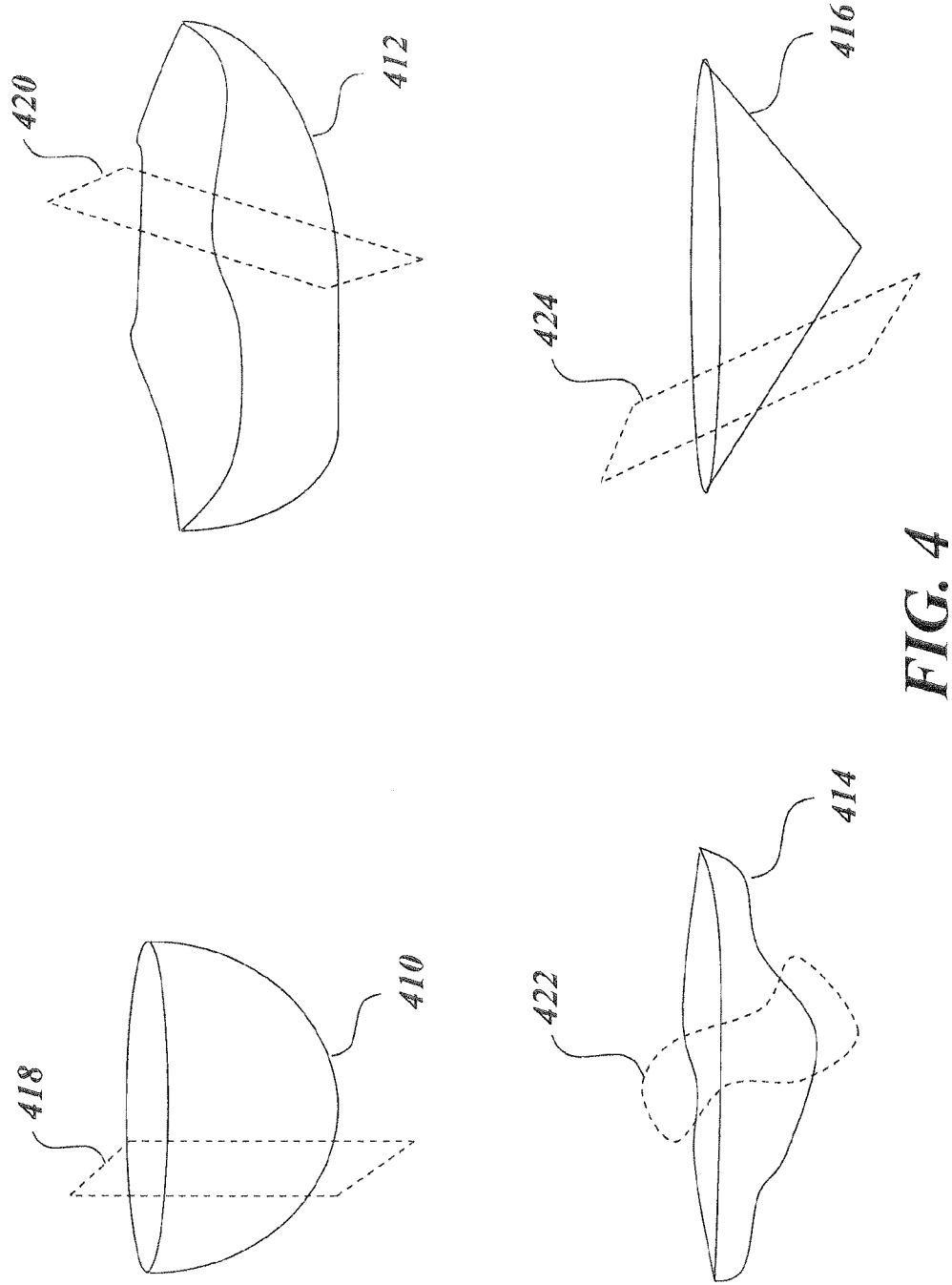
FIG. 4 is a diagrammatic illustration of various examples of open sided bowls, according to aspects of the present invention.

It is known that a bowl is a generally circular shape that has a continuous circular edge with no specified end. An "open sided bowl," as used herein, is a shape generally resembling that of a bowl that has a disruption in the generally circular edge such that the generally circular edge tips down and away from the bowl, effectively lowering a wall of the bowl on one side, in a manner that would allow a fluid hypothetically contained within the bowl to spill out. An open sided bowl does not, for example, have a perfectly circular rim (at least for the reason that one portion of the rim is tipped down and away, thus disrupting the otherwise generally circular or closed shape of a rim in a conventional bowl). The open sided bowl, as referred to herein, maintains the bowl shape for at least about 50% of the perimeter, while the portion of the generally circular edge that tips down and away from the bowl shape can make up some portion of the remaining approximately 50% of the perimeter. As depicted herein, the bowl shape is generally maintained to form about half of (i.e., about 50%) of the more conventional bowl shape, while the "open side" makes up generally about the other half. Those of skill in the art will appreciate that the specific percentages of how much of the wall of the open sided bowl is configured similar to a conventional circular bowl, and how much of the wall of the open sided bowl is tipped down can vary considerably within the parameters of the present invention (i.e., 25:75, 30:70, 35:65, 40:60, 45:55, 50:50, 55:45, 60:40, 65:35, 70:30, 75:25, or the like). The open sided bowl configuration is intended to describe a configuration wherein the end of the body 100 that forms the open sided bowl is an end that has the generally raised up and cupped or bowled form that opens to the remaining portion of the body 100 in the continuous, smooth transitional, manner depicted in the present disclosure. For example, FIG. 4 depicts four example shapes 410, 412, 414, and 416 generally resembling the shape of a bowl. It will be understood from these drawings, namely FIGS. 1A, 2, 3A and 4, that, in general, symmetry, uniform curvature, a lack or presence of straight edges, a lack or presence of sharp points, and other related geometrical features are not required in order for a shape to generally resemble that of a bowl. An open sided bowl, as described herein, can be formed by tipping downward the edge of any of the shapes of FIG. 4. For example, the shapes can be tipped downward or cut along a vertical plane such as plane 418, along a slanted plane such as plane 420 or plane 424, or along a non-planar area such as surface 422. The cut can occur at a midpoint or at any other point between the two ends. The two shapes resulting from such a cut are both open sided bowls. Accordingly, it can be appreciated from FIG. 4 that the term "open sided bowl" is in no way limited to the specific illustrative structure depicted in FIGS. 1A through 3B, or even to the examples provided in FIG. 4. An "an open sided bowl" as understood by one of skill in the art can encompass any such illustrative bowl shapes, in addition to others not specifically illustrated herein, as to depict all such possible bowl shapes would not be reasonably expected or required by those of skill in the art for a sufficient understanding of the configuration of the present invention.

Returning to FIGS. 1A, 2, and 3A, the banked region 118 can be curved and banked. The curved line 132 of FIG. 1A depicts the non-uniform manner in which the banked region 118 can be curved in the transverse plane. As shown in the figures, the banked region 118 can be curved in a convex direction. Alternatively, the banked region 118 can be curved both convexly and concavely, or simply concavely, depending on the particular medical application and the intended target site. The banked region 118 also possesses a longitudinal bank, in a manner so as to extend up from the substantially planar area 114. An upward curving line 134 of FIG. 2 depicts the non-uniform manner in which the banked region 118 can be banked. Alternatively, the substantially planar area 114 can occupy a larger or smaller area on the body 100 than as depicted in FIGS. 1A, 2, and 3A. Accordingly, the substantially planar area 114 can extend along the body 100 to additional segments of the perimeter 110. For example, FIG. 3B depicts an embodiment where the banked region 118 only extends along a portion of a length of the body 100 and the substantially planar area 114 extends to a segment of the perimeter 110 near the back (i.e., into the page as depicted in FIG. 3B). Yet other alternatives are possible. In general, the banked region 118 can extend along all or some portion of a length of body 100.

When measured with respect to the substantially planar area 114, the average upward slope of the banked region 118 can be smaller at a portion nearer to the substantially planar area 114. Said differently, the slope of the banked region 118 can increase moving up the banked region 118. For example, the banked region 118 can be characterized by an average longitudinal slope of about 0° (i.e., no slope), about 5°, about 10°, about 15°, about 20°, about 25°, about 30°, about 35°, about 40°, about 45°, about 50°, about 55°, about 60°, about 65°, about 70°, about 75°, about 80°, about 85°, or any slope, e.g., falling therebetween. Furthermore, the banked region 118 can be characterized by an average radius of curvature in a transverse plane of about 0 inches (i.e., no curvature), 0.5 inches, 1 inches, 1.5 inches, 2 inches, 2.5 inches, etc., and any average radius of curvature, e.g., falling therebetween. In general, the average longitudinal slope and the average radius of curvature in a transverse plane of the banked region 118 can be any suitable value, as would be appreciated by one of skill in the art upon reading the present specification.

Figure 1B:
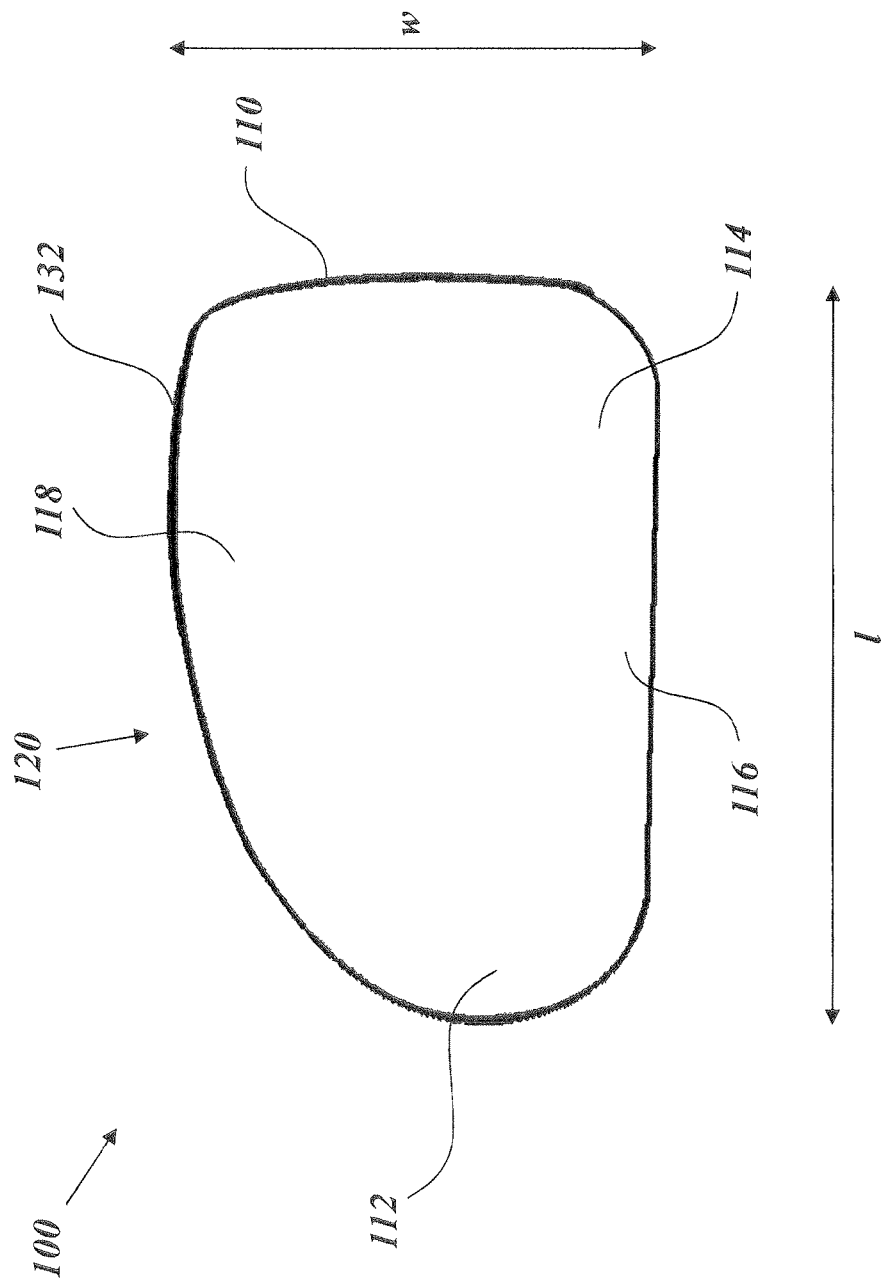
FIG. 1B is a top view of a three-dimensional shaped prosthesis with an arched region that is substantially non-curved transversally, according to embodiments of the present invention.

As depicted in FIG. 3A, the arch region 116 can slope up from the substantially planar area 114 in a shape generally resembling that of an "S". Other shapes and curvatures are possible, having a higher or lower number of inflection points, but may impact the ultimate functionality of the device. The arch region 116 also can curve transversally, as depicted in FIG. 2, to form an arch or hood-like structure. Alternatively, the arch region 116 can have substantially no curvature in the transverse plane. For example, FIG. 1B depicts one example embodiment where the arch region 116 substantially does not curve in the transverse plane. As depicted in the figures, the radius of curvature and the slope of the arch region 116 are not uniform in the illustrative embodiment. As examples, the average longitudinal slope of the arch region 116 can be about 0° (i.e., no slope), about 5°, about 10°, about 15°, about 20°, about 25°, about 30°, about 35°, about 40°, about 45°, about 50°, about 55°, about 60°, about 65°, about 70°, about 75°, about 80°, about 85°, or any other slope, e.g., falling therebetween. Furthermore, the average radius of curvature can be 0 inches (i.e., no curvature), about 0.5 inches, 1 inches, 1.5 inches, 2 inches, 2.5 inches, etc., and any average radius of curvature falling therebetween. In general, the average longitudinal slope and the average radius of curvature in a transverse plane of the arch region 116 can be any suitable value, as would appreciated by one of skill in the art upon reading the present specification. While illustrative dimensions are provided herein, these dimensions in no way limit the present invention. One skilled in the art will appreciate that the specific sizes and dimensions can be selected on a case by case basis and optimized according to the intended usage, depending upon the particular anatomical region to be treated by the prosthesis.

The open sided bowl 112 and the substantially planar area 114 are coupled by a transitional area 120. As used herein, a "transitional area" is an area that provides at least one path connecting or coupling two areas or portions. However, it should be noted that two areas or portions coupled or connected by a transitional area can be additionally coupled or connected directly to each other (i.e., meaning that the two areas are abutting or contiguous). Accordingly, the transitional area of FIG. 2 includes at least the arch region 116 and the curved banked region 118. The arch region 116 and the curved banked region 118 can be coupled together, either directly (i.e., abutting) or indirectly (e.g., via a transitional area).

The full path of the perimeter 110 can be traced, beginning at an edge of the arch region 116 and moving in a clockwise direction when viewed from above. Particularly, when following the perimeter 110 in this manner, the arch region 116 leads to the open sided bowl 112, which leads to the curved and banked region 118, which leads to the substantially planar area 114, which leads back to the arch region 116. This closed loop completes the path of the perimeter 110 and delineates the relative positions of the various portions, regions, and areas described herein.

A preformed flexible implantable prosthesis having the body depicted in FIGS. 1 through 3 in accordance with the present invention can be configured and additionally shaped and dimensioned to particularly meet the shape of a particular anatomical site, as would be appreciated by one skilled in the art. While an illustrative embodiment described herein provides an implantable prosthesis shaped and dimensioned to accommodate the specific structure of a laparoscopic inguinal region, other anatomical regions are possible and contemplated by the present invention, as would be appreciated by one skilled in the art.

Figure 5:
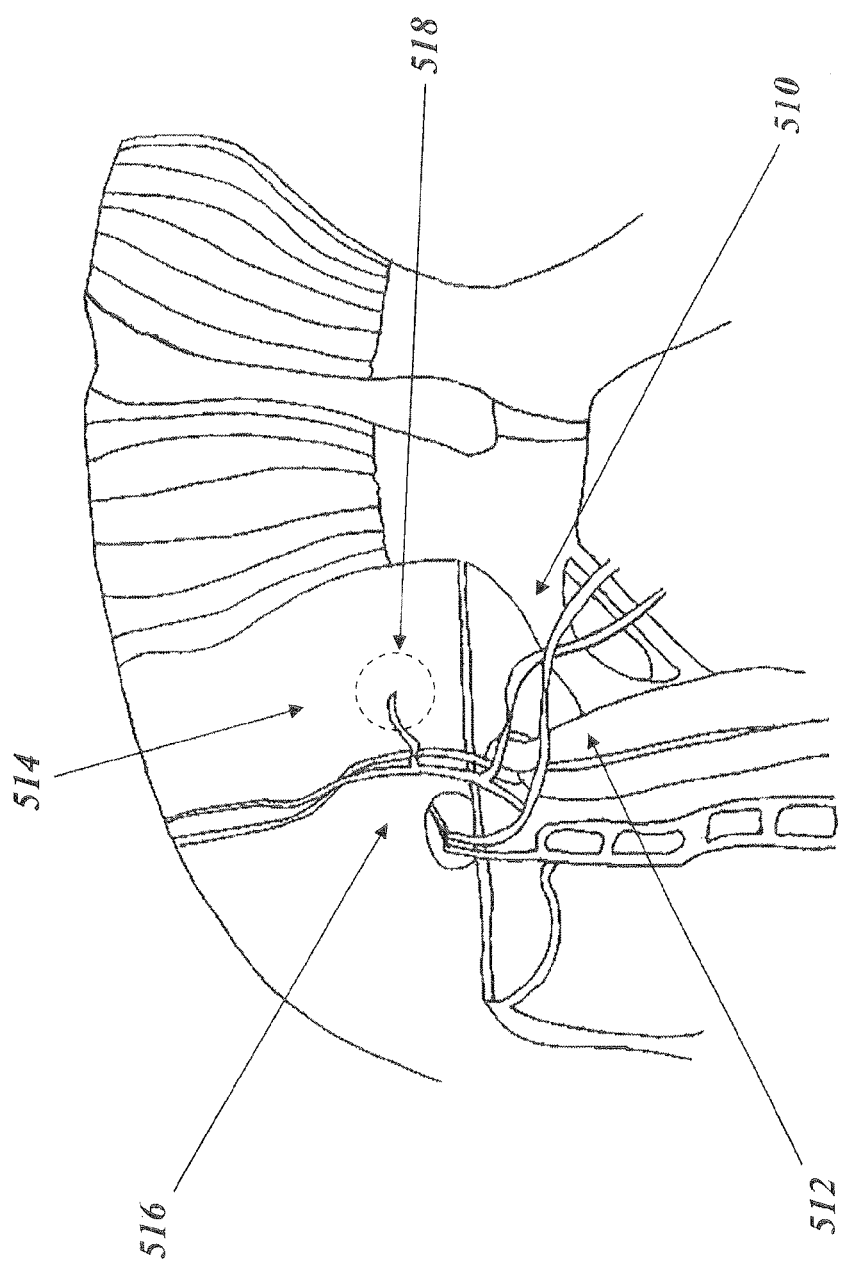
FIG. 5 is a diagrammatic illustration of a left inguinal region of a patient, where a three-dimensional shaped prosthesis of the present invention may be implanted.

An example of a laparoscopic inguinal region is shown in FIG. 5. Specifically, the region includes a Cooper's ligament 510, external iliac vessels 512, an abdominal wall 514, and a lateral extraperitoneal space 516. In an illustrative embodiment, the prosthesis depicted in FIGS. 1 through 3 is sized, dimensioned, and configured to accommodate the anatomical region depicted in FIG. 5, specifically for the purpose of treating/preventing an existing or future defect such as an inguinal hernia. In particular, the substantially planar area 114 can provide a suitable surface for fixation (e.g., via suturing or in-growth of surrounding tissue) of the prosthesis to the Cooper's ligament 510 and/or the abdominal wall 514. The open sided bowl 112 can substantially match or conform to the contour of the lateral TEP space 516, as depicted in the figures and would be appreciated by one of skill in the art. The arch region 116 can be sized and dimensioned to accommodate the external iliac vessels in such a way as to avoid placing significant pressure upon them.

As an example embodiment, when adapted for inguinal hernia repair, the substantially planar area 114 can have a surface area that occupies about twice a surface occupied by the arch region 116. Furthermore the arch region 116 and the curved and banked region 118 can have surface areas that are substantially equal to one another. In three example embodiments implemented for covering an area 518 of a direct defect, the body 100 can have dimensions of 9.0×14.5 cm, 10.5×16.0 cm, 12.0×17.0 cm (given as length l by width w, i.e., as depicted in FIG. 1B).

One of skill in the art will appreciate that these values in no way limit embodiments of the present invention to these specific illustrative dimensions and proportions. The desired size, proportions, and surface areas, can be adjusted as necessary based on the shape of the particular target site, the uniqueness of a particular patient or group of patients, and other related concerns that are known in the art. For example, one of skill in the art will appreciate that patients of different sizes may require prostheses that are differently sized.

The body 100 can be constructed from a biocompatible material, and can be formed from and include a mesh, which can include coated and/or uncoated mesh materials. If the prosthesis is to be affixed in a patient via in-growth, then the mesh can be sufficiently porous to promote tissue in-growth, such that the strands of the mesh are colonized by the surrounding cells in which it is embedded. Preferably, the mesh is biocompatible with the tissues and media of the inguinal space. The mesh can be a flexible material having substantially uniform properties. Alternatively, the mesh can possess one or more sections having differing values for tension and/or rigidity.

Figure 6A:
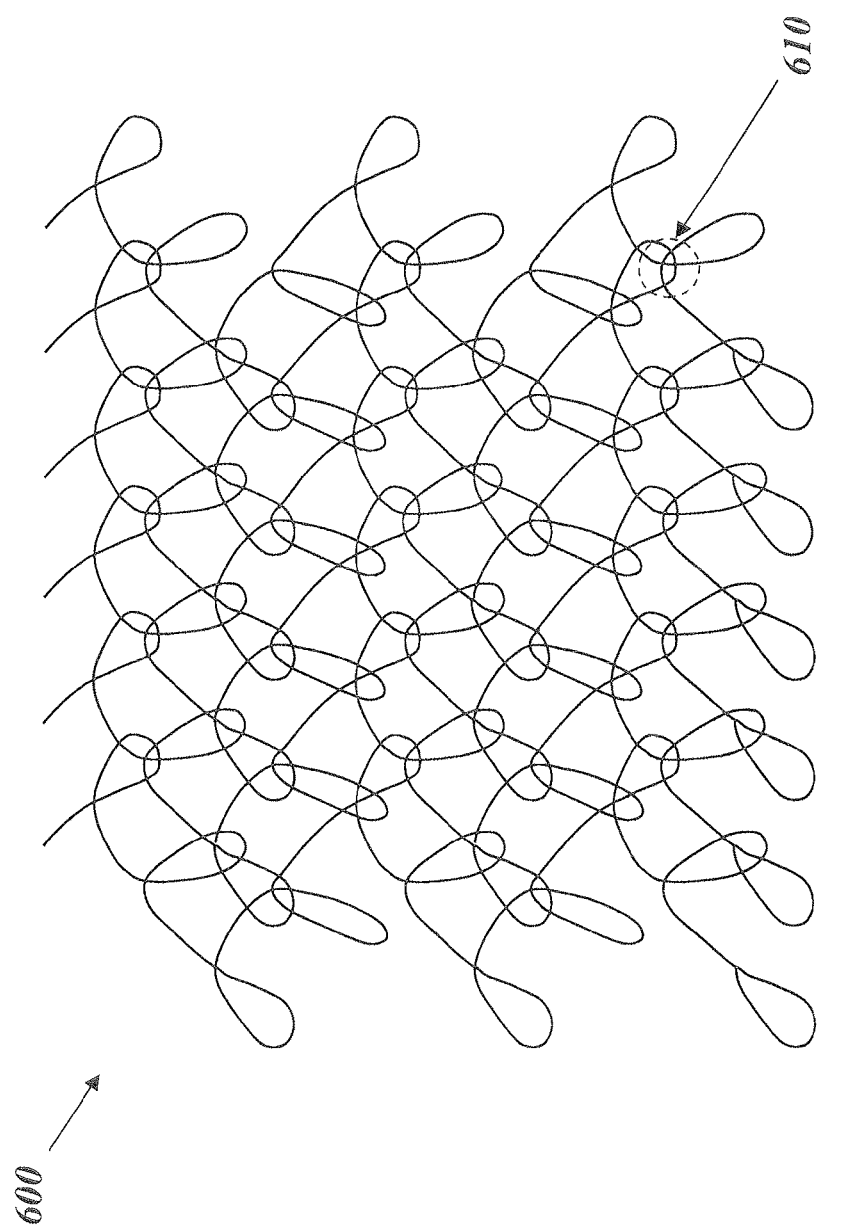
FIG. 6A is a diagrammatic illustration of a material comprising strands forming a plurality of intersections, according to embodiments of the present invention.
Figure 6B:
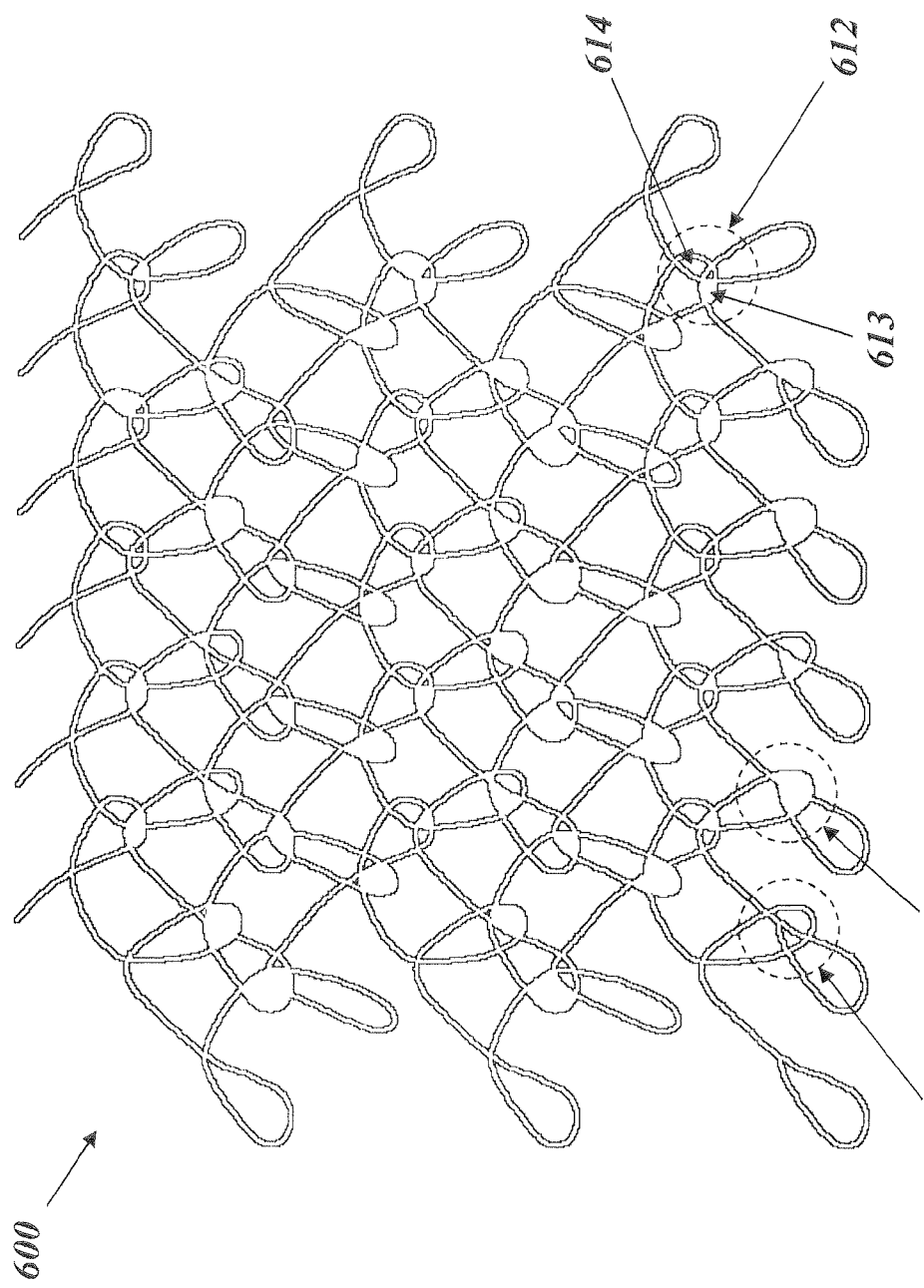
FIG. 6B is a diagrammatic illustration of the mesh of FIG. 6A with a coating at least partially disposed in the intersections of the material, according to embodiments of the present invention.

An exemplary mesh 600 is depicted in FIGS. 6A and 6B. FIG. 6A shows an uncoated mesh 600. In general, the mesh 600 may be a semi-permeable structure that includes connected strands of flexible or ductile material. As would be understood by one of skill in the art, the strands of the mesh 600 can be connected using a number of different configurations and methodologies, including but not limited to inter-looping, weaving, braiding, knotting, knitting, and the like, as well as being formed directly into a mesh or grid-like pattern. The mesh 600 includes a plurality of intersections 610. "Intersections," as used herein, is not limited to any single or particular type of intersection. Rather, "intersections" can include knits, stitches, braids, knots, loops, weaves, substantially seamless junctions, generally known intersections in accordance with industry standard interpretations of said term, and other known intersections in grid-like mesh patterns. It should be noted that when the intersections are formed by multiple strands or threads in such a way that the multiple strands or threads can move relative to each other, the addition of a coating can provide reinforcement to such strand or thread intersections as described herein. In accordance with an exemplary embodiment of the present invention, the mesh 600 is a polypropylene mesh.

FIG. 6B depicts the mesh 600 of FIG. 6A further including a coating. In particular, the mesh may be coated with a fatty acid based material, including a non-polymeric hydrolysable bioabsorbable cross-linked fatty acid based material. The coating can be a coating derived from eicosapentaenoic (EPA) and/or docosahexaenoic (DHA) fatty acids. In some of the embodiments of the present invention, the mesh is coated with a coating derived from fish oil, such as an omega-3 fatty acid. The coating derived from fish oil or omega-3 fatty acid can be partially cured or fully cured. The coating can be a non polymeric cross linked material or the coating can be a polymeric cross linked material, with corresponding advantages or disadvantages of the coating material as understood by those of skill in the art. The cross-links can be formed of ester bonds, lactone bonds, or both. Particularly illustrative examples of coated polypropylene meshes suitable for use with illustrative embodiments of the invention include, but are not limited to, C-QUR™ Mesh and/or C-QUR FX™ Mesh, manufactured by Atrium Medical Corporation of Hudson, N.H.

In the illustrative embodiment of FIG. 6B, the coating at least partially fills the intersections 610 of the mesh 600. More specifically, the mesh 600 can include partially filled intersections 612, completely filled intersections 616, and/or unfilled intersections 618. As depicted in the figure, partially filled intersections 612 can include at least one filled portion 613 and at least one unfilled portion 614. In illustrative embodiments, the mesh 600 is coated with about 10-15 mg of coating per square inch of the mesh 600. Other coating quantities are possible. In illustrative embodiments, greater than half of all of the intersections 610 are at least partially filled with coating. For example, the percentage of the intersections 610 that are at least partially filled with coating can be about 50%, about 55%, about 60%, about 65%, about 70%, about 75%, about 80%, about 85%, about 90%, about 95%, about 100%, or any other percentage, e.g., any percentage falling therebetween. Accordingly, in some embodiments, all of the intersections 610 of the mesh 600 are at least partially filled with a coating. In yet other embodiments, all of the intersections 610 of the mesh 600 are completed filled. In some embodiments, less than 50% of the intersections 610 of the mesh 600 can be at least partially filled with coating. Generally, higher amounts of coating and/or higher percentages of at least partially filled intersections 610 can result in greater stiffness of the mesh 600 and greater stiffness of the resulting implantable prosthesis.

In accordance with an illustrative embodiment of the present invention, a coated implantable prosthesis includes a coated mesh such as the coated mesh 600 depicted in FIG. 6B. The coated implantable prosthesis can be preformed to have a contoured three-dimensional shape and further can be preformed to have the contoured three-dimensional shape of any of FIGS. 1A through 3B. Furthermore, the preformed coated prosthesis can be coated so as to independently assume its three-dimensional shape.

The coating on the mesh 600 can have a sufficient thickness to serve as a physical protective layer between surrounding tissue and the surface of the mesh structure on the coated prosthesis. In the illustrative embodiment, the coating can have a thickness that is between about 0.006 inches and about 0.019 inches thick. However, other thicknesses are possible. When constructed in this manner, the protective layer can provide protection particularly during and upon initial implantation, such as against abrasions due to surrounding tissue being pressed or rubbed against the protective layer and/or mesh. In such circumstances the coating can flatten out or smooth out the surface of the mesh, to reduce or eliminate the potential for abrading nearby tissue. Over time, the bioabsorbable coating can slowly be absorbed by the surrounding tissue and fluids, and tissue in-growth is allowed to penetrate through the mesh, in the place of the bioabsorbable coating. As such, the underlying mesh structure is eventually engulfed by tissue in-growth, which again flattens or smoothes out the mesh structure relative to nearby tissue, eliminating the potential for abrasions.

In accordance with an illustrative embodiment of the present invention, the coating on the preformed coated prosthesis in part enables the prosthesis to achieve a substantially uniform rigidity. For example, the rigidity (e.g., flexural rigidity, for example as measured by a Shirley Stiffness Tester) can be greater than about 150 mg×cm. In one illustrative embodiment, the rigidity of the preformed coated prosthesis is about 400 mg×cm. As yet further non-limiting possibilities, the preformed coated prosthesis can have any rigidity in the range of about 400 mg×cm to about 800 mg×cm. Other values of rigidity can be used that enable the implantable prostheses according to the present invention to achieve invertibility and/or the property of independently assuming a predetermined three-dimensional shape even subsequent to at least one fold, etc. (e.g., without the use of a rigidified perimeter). In general, the body can have a sufficient flexibility to deform under at least a minimum predetermined force typically experienced during implantation against a muscle or tissue wall, as would be appreciated by one of skill in the art.

The use of a coated mesh as described herein has been found to increase the capacity of an implantable prosthesis to the exhibit shape retention, or to maintain a shape memory. It can be appreciated that the term "shape memory," when referring to the characteristic of exhibiting shape retention or of independently assuming a predetermined three-dimensional contoured shape, should not be misinterpreted as necessarily indicating shape memory material or any other particular material that is not explicitly described. Rather, in some embodiments, coated meshes can independently assume a predetermined three-dimensional shape by virtue of having coating disposed in the intersection, which causes a preference for relative orientation of the loops and strands relative to each other (thus causing a preference for the predetermined three-dimensional contoured shape that results when each strand and loop is in such relative arrangement). Said differently, the three-dimensional contoured shape is maintained by interaction of the plurality of intersections with each other imparting structure to form and maintain the three-dimensional contoured shape configuration. In illustrative embodiments, a flexible preformed prosthesis independently assumes a three-dimensional contoured shape without the need for or inclusion of a perimeter that is rigidified relative to the remainder of the prosthesis, and that dictates the shape of the attached more flexible material that is not rigidified. In general, the predetermined three-dimensional contoured shape can be the shape described with reference to any of FIGS. 1A through 3B.

What is meant by "independently" when referring to the assumption of the predetermined shape is that there is an absence of an external bending or collapsing force required for application against the prosthesis for it to independently assume its predetermined three-dimensional contoured shape. For example, prostheses according to embodiments of the present invention can fold and bend in response to forces applied thereto by lumen walls, etc., as typically experienced during implantation, and to subsequently independently unfold into the predetermined three-dimensional contoured shape upon reaching the target site. Thus, the exemplary prostheses according to embodiments of the present invention can be configured to fold, bend, become rolled, or will otherwise collapse or yield in the presence of certain applied force. However, subsequent to the release of such forces, the preformed prosthesis can independently assume its contoured, predetermined three-dimensional shape, without requiring a rigidified perimeter or border. In embodiments where the preformed prosthesis can be designed to substantially re-assume a contoured, predetermined three-dimensional shape subsequent to implantation, this feature can improve ease of handling, e.g., by a surgeon inserting the prosthesis into a patient. The preformed prosthesis can be configured to assume a contoured, predetermined three-dimensional shape subsequent to at least one iteration of a folding action, a bending action, etc. In an illustrative embodiment, a preformed coated prosthesis can withstand at least two iterations of folding, bending, rolling, etc. and still assume its predetermined shape. In other words, an illustrative preformed coated prosthesis can be folded, etc. at least two times and still assume substantially the same predetermined shape.

The ability of the flexible preformed coated prostheses to assume and maintain a contoured predetermined three-dimensional shape even subsequent to at least one bending action, folding action, rolling action, collapsing action, etc., and any combination thereof, can be attributed to the feature of the coating that at least partially fills the intersections, thus causing a preference for the loops and strands of the mesh to be in a particular arrangement relative to each other. This structural feature, as described herein, results in the functional effect of configuring the shape of the mesh 600 in a manner that enables the preformed coated prosthesis to assume (e.g., "spring back") a predetermined three-dimensional contoured shape even subsequent to at least one fold, bend, roll, etc., and any combination thereof. Said differently, it is the combination of the forces supplied by the intersections of the mesh structure that imparts the required force to form and maintain the three-dimensional contoured shape without requiring a rigidified perimeter or other form of structure to maintain the three-dimensional contoured shape of the present invention. In an illustrative embodiment, the predetermined three-dimensional contoured shape of such a preformed coated prosthesis is the shape described with reference to any of FIGS. 1A through 3B.

In example embodiments, the prosthesis can unfold or otherwise re-assume its contoured predetermined three-dimensional shape upon the introduction of heat, energy, light, and the like (e.g., body heat, where the prosthesis is formed of a shape memory material). In such embodiments, the use of a coating may not be necessary, as would be appreciated by one of skill in the art. In some embodiments, a heat welding, thermoforming, or other similar process can cause the individual loops and strands to stick to each other, be permanently bent, in a preferred relative orientation, thus causing the larger shape of the prosthesis to have a preferred contoured predetermined three-dimensional shape. Other embodiments and equivalent materials for enabling the feature of independently assuming a contoured predetermined three-dimensional shape are contemplated within the scope of the present invention.

The coating described herein enables prostheses according to illustrative embodiments of the present invention to overcome significant drawbacks in existing mesh technology. In particular, embodiments of the present invention can distinguish over existing implantable preformed prostheses by not requiring a rigidified peripheral edge or perimeter to independently assume a predetermined three-dimensional shape, even subsequent to at least one folding action, etc. Due to the rigid peripheral edge of conventional devices, many existing prostheses are prohibited from being cut, trimmed, or otherwise removed or altered, because to cut-out or remove the rigidified edges is to remove the ability of the prosthesis to independently assume a contoured three-dimensional shape. Thus, a surgeon is unable to customize the shape or size of such a prosthesis prior to implantation into a patient. It has been suggested in the art that the feature of not requiring trimming is a benefit given the greater ease with which a prosthesis can be prepared for implantation. However, Applicants have recognized that this feature can pose a significant problem for the success and effectiveness of a preformed implantable prosthesis, given that different patients possess different body sizes and exhibit different anatomical proportions (thus, a one-size fits all approach does not work in all cases) and that this is a significant concern among consumers of such prostheses. The ability to trim and re-shape the outer profile or perimeter shape of the prosthesis, without thereby removing the structure that causes the remaining portions of the prosthesis to maintain a three-dimensional contoured shape, provides a significant benefit to the implementation of such a prosthesis in a patient. This benefit is directly brought about in in view of the developments of the present invention which enable such trimming to occur without sacrificing the ability of the device to resume or assume its predetermined three-dimensional contoured shape even after being trimmed.

Accordingly, the present invention incorporates the recognition that the capability for trimming may be desirable and in some cases beneficial, in order to enable custom fits for patients having anatomical regions of varying sizes and proportions. Illustrative embodiments according to the present invention solve the problem of an inability to trim or otherwise remove all or part of the perimeter by providing a coating disposed at least partially within the intersections of the mesh. The coating, as described herein, provides the entire preformed prosthesis with a suitable rigidity to maintain a contoured, predetermined three-dimensional shape, as previously described herein. Thus, an outer portion of the mesh extending along the entire perimeter and thereby including a perimeter can have about the same average rigidity as an inner portion that is surrounded by the perimeter. Furthermore, the rigidity of the perimeter, the outer portion, and the inner portion can be substantially equal and uniform, such that the outer portion, the inner portion, and the perimeter all include substantially the same substantially uniform rigidity. In illustrative embodiments, the body does not comprise a perimeter that is rigidified relative to a remainder of the body. In further illustrative embodiments, the rigidity of the mesh is uniform across all portions of the body 100, and is about 400 mg×cm to about 800 mg×cm. To be clear, the absence of a rigidified perimeter relates to rigidified perimeters that are required to for the remaining portions of the prosthesis to maintain a three-dimensional contoured shape. Rigidified perimeters that do not impart such additional structure support for the remaining portions of the prosthesis (i.e., rigidified perimeters having a different function and purpose) are not necessarily what is being referred to in the context of the present invention. The present invention can maintain three-dimensional contoured shapes without requiring a rigidified perimeter.

Figure 7A:
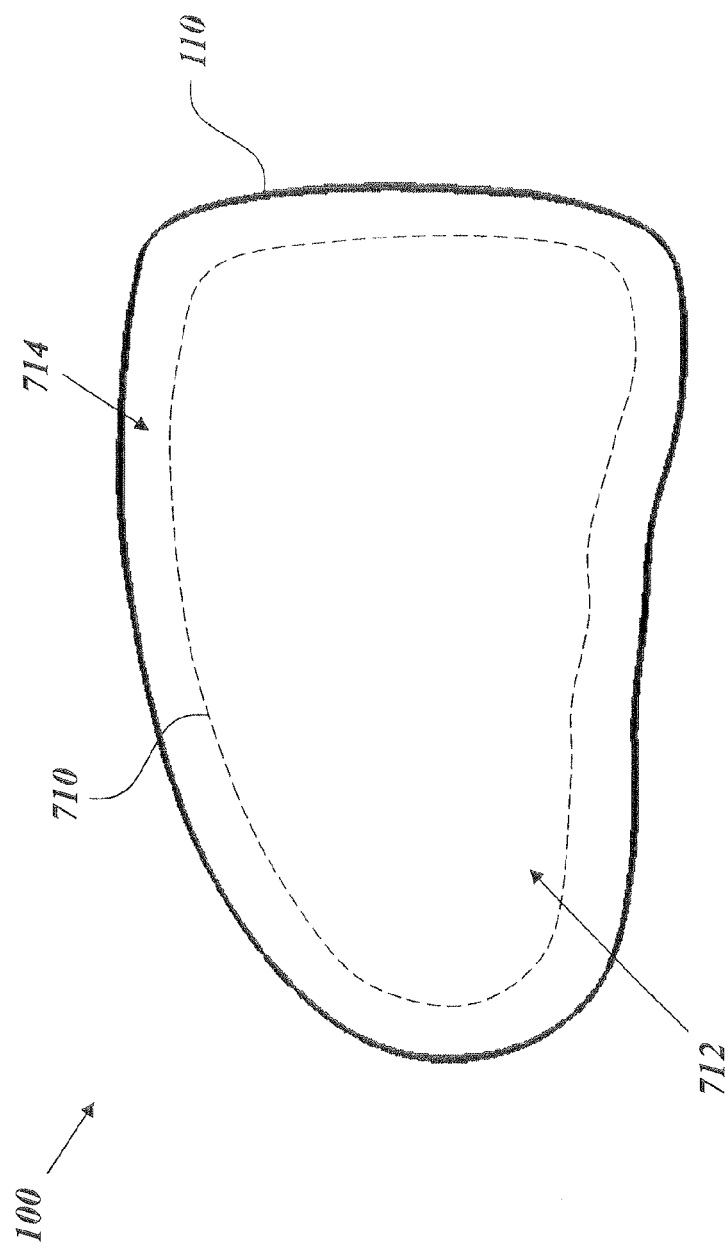
FIG. 7A is a diagrammatic illustration of a prosthesis made from a continuous, single piece of mesh and having an inner portion and a perimeter surrounding the inner portion, according to embodiments of the present invention.
Figure 7B:
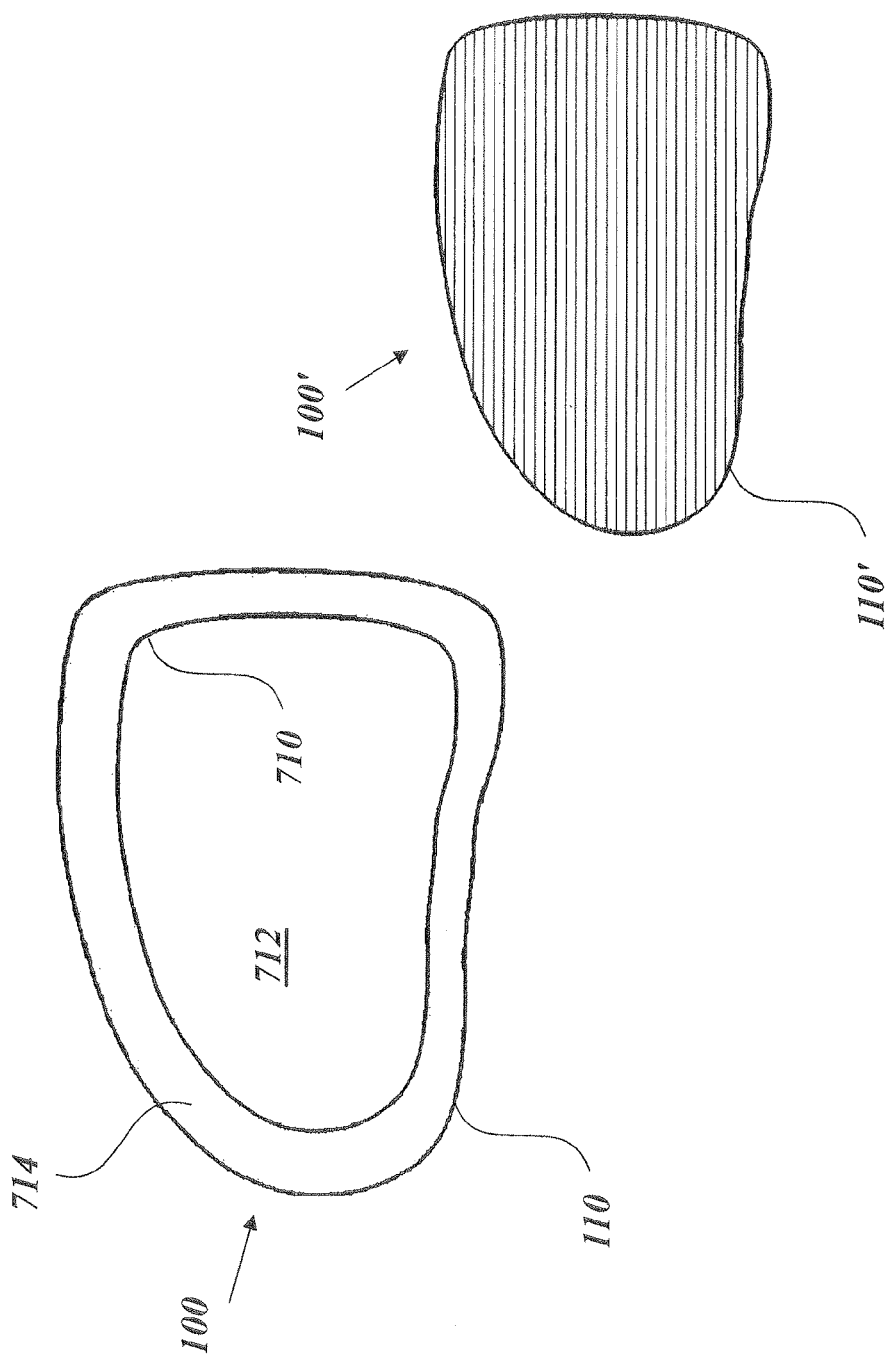
FIG. 7B is a diagrammatic illustration of the prosthesis of FIG. 7A maintaining a three-dimensional contoured shape despite the perimeter portion being trimmed off or otherwise removed, according to embodiments of the present invention.

For example, as depicted in FIG. 7A, the body 100 of the prosthesis can be trimmed along an inner line 710 to remove an outer portion 714 of the body 100, such that only an inner portion 712 remains. Upon trimming the body 100 along the inner line 710, a smaller body 100' having a reduced size and a reduced perimeter 110' is formed, as depicted in FIG. 7B. Notably, the three-dimensional contoured shape of the body 100' of FIG. 7B is substantially the same as the three-dimensional contoured shape of the inner portion 712 of the body 100 of FIG. 7A in terms of its three-dimensional contoured shape. Said differently, in certain illustrative embodiments according to the present invention, the act of removing one or more outer portions of the body 100 does not substantially affect the three-dimensional contoured shape of the remaining non-removed portion of the body 100. Rather, the subset of the three-dimensional contoured shape contributed by the inner portion 712 remains substantially the same regardless of whether a perimeter 110 has been removed, e.g., in a trimming procedure. This enables the body 100 to be custom fit by a surgeon prior to, or during, implantation (e.g., through a trimming procedure). The prosthesis according to illustrative embodiments of the present invention thus can be adapted to easily accommodate differently sized patients, while beneficially maintaining a three-dimensional contoured shape.

In the example of FIG. 7A, the inner portion 712 does not contact the perimeter 110 of the body 100. However, the same effects described herein can be achieved by only trimming along a portion of the perimeter 110. Furthermore, one of skill in the art will appreciate that a wide variety of other procedures can be used for removal of portions of the body 100 to accommodate differently sized patients.

The coated mesh as described herein additionally has been found to enable a flexible, preformed prosthesis having a three-dimensional contoured shape to be inverted between two orientations that are substantially mirror images of each other. For example, such a preformed coated prosthesis can be invertible so as to independently assume either a left orientation or a right orientation that are substantially mirror images of each other. The predetermined three-dimensional contoured shape of the preformed prosthesis can be any one of the shapes described with reference to FIGS. 1A through 3B. In particular, the body 100 depicted in the figures can be the body of a preformed coated prosthesis, as described herein, that is in a right orientation so as to fit the inguinal region of the right side of a patient. Given its ability to invert, such an invertible coated prosthesis can also be configured to independently assume a shape that is substantially a mirror image of the body 100. Such a shape of the body 100 can represent a left configuration for fitting the inguinal region of the left side of a patient.

Figure 8:
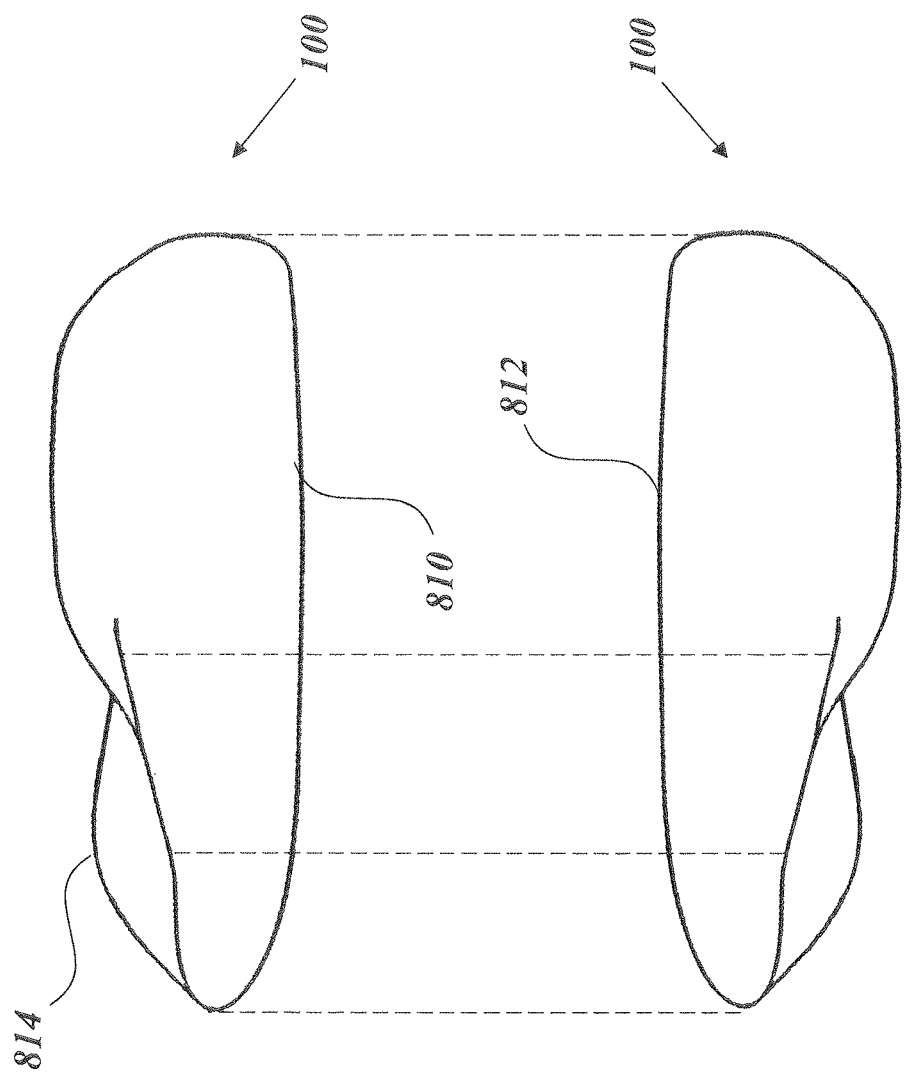
FIG. 8 is a diagrammatic illustration of an invertible prosthesis that is configured to independently assume either an original orientation or a substantially mirror image orientation, and which is able to be inverted between the two orientations.

As an illustrative example, FIG. 8 depicts the body 100 of FIG. 2 in an original orientation 810 and a substantially mirror image orientation 812. The body 100 can be inverted from the original orientation 810 to the substantially mirror image orientation 812, for example by pressing down on a convex curvature such as surface 814 with a sufficient pressure to invert the curvature such that it becomes concave, thereby forming a substantially mirror image of the original orientation 810. Once the entire body 100 has been fully inverted to the substantially mirror image orientation 812, the preformed prosthesis will independently assume the substantially mirror image orientation 812. In this example, the body 100 can be particularly sized and configured for inguinal regions, such that the original orientation 810 is a left orientation for treatment of the left inguinal region, and further such that the substantially mirror image orientation 812 is for treatment of the right inguinal region.

A coated three-dimensional shape of the prostheses may be preformed according to a thermoforming process. In one illustrative embodiment, the thermoforming procedure includes placing a sheet of mesh into a template such as a mold having the desired shape for the prosthesis, heating the mesh in the template at a predetermined temperature for a predetermined time (e.g., in a heat source such as an oven), and subsequently cooling the mesh in the mold, such as by removing from the heat source and applying an air flow having a predetermined temperature, for a predetermined period of time. In yet another embodiment, the mold can be heated in a heat source (e.g., an oven), and removed from the heat source (e.g., after a predetermined amount of time, once the mold has reached a predetermined temperature, etc.). The mesh then can be placed in the heated mold, for a predetermined amount of time. In such embodiments, the mold can be made to retain a sufficient quantity of heat for a sufficient time to form the mesh into the particular desired three-dimensional shape (e.g., the three-dimensional shape of any of FIGS. 1A through 3B).

Figure 9:
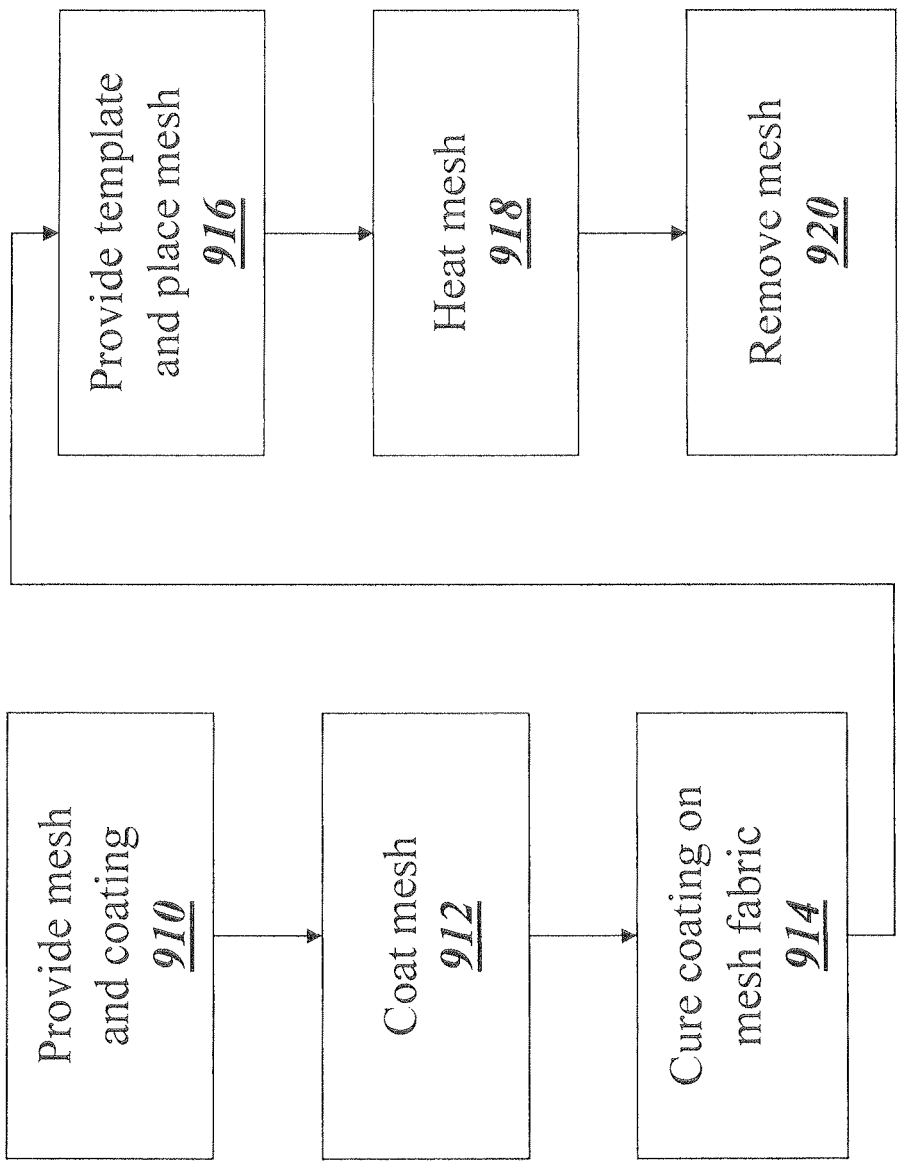
FIG. 9 depicts an illustrative method for manufacturing implantable prostheses according to embodiments of the present invention.

For example, FIG. 9 illustrates with greater detail one exemplary method for manufacturing a preformed coated prosthesis having a three-dimensional shape according to embodiments of the present invention. First, in step 910, a suitable mesh and a suitable coating are provided, such as the mesh and coating described herein with reference to an illustrative embodiment of FIG. 6B. Next, in step 912, the mesh is coated. The coating can be applied by spraying, for example. Any other suitable method of applying a coating that is known in the art may be used, for example, dipping, brushing, pumping, direct deposit of a predetermined amount of coating via a conduit connected to a fluid reservoir, other known methods of coating, and any combination thereof. In an illustrative embodiment about 10-15 mg of coating is applied per square inch of mesh. In step 914, if so desired, the coating on the mesh is cured to produce cross linking of the coating, such as a fish oil coating or coating comprising a fatty acid based material. As an illustrative example, the coating can be cured by exposing the coating and the mesh to a temperature in the range of about 50° C. to about 121° C. for a period of time in the range of about 8 hours to about 48 hours. Other curing times and temperatures are possible. In some embodiments of the present invention, the coating can be cured to produce cross linking prior to coating the mesh (i.e., steps 912 and 914 can be reversed). In some embodiments of the present invention involving uncured coatings, step 914 is eliminated altogether.

In step 916, a template is provided having a particular desired shape and the coated, cured mesh is placed in the provided template. The template can include a mold. The mold can be made from stainless steel, aluminum, or any other heat conductive metal. In particular, the mold can be situated in a press, such as a Carver press. If a press is used, generally the pressure applied by the press should be maintained as low as possible, as would be appreciated by one of skill in the art. In some embodiments additional pressure beyond a weight of the mold is not applied. For example, the mold can weigh about 1-2 pounds, and can apply a pressure of about 30 psi. One of skill in the art will appreciate that these values are illustrative and in no way limiting of the present invention.

Once placed, the mesh is heated at one or more predetermined temperatures for one or more predetermined times (step 918). As examples of thermoforming schedules, the mesh can be heated in various stages or under uniform conditions. The template can be preheated to a particular predetermined temperature prior to placement of the mesh. In an illustrative embodiment the template is preheated to a temperature of about 140° C., and the mesh is placed in the preheated template for a period of 20 minutes. Subsequently, the mesh can be removed (step 920) from the template after some predetermined amount of time has passed. For example, the mesh can be heated in an oven in step 918 for about 20 minutes at a temperature of about 140° C., and then removed from the oven and allowed to cool for about 20 minutes until it is removed from the template in step 920. Alternatively, the mold can be heated to about 140° C. in an oven and removed from the oven, and then the mesh can be placed in the mold in step 918 where it remains for about 10 minutes as the mold cools and is then removed in step 920. As still further non-limiting examples, the mesh can be heated at any temperature in an illustrative range of about 130° C. to about 800° C., for any period in an illustrative range of about 0.1 minutes to about 20 minutes. Accordingly, the mesh can heated at high temperatures for very short periods of time, or for longer periods of time at relatively lower temperatures.

The mesh optionally can undergo a cooling process, either before or after removal (step 920). For example, an air flow at a predetermined temperature can be applied to the mesh for a predetermined period of time to cool the mesh, or the mesh can be cooled by refrigeration, passive cooling, placement on a highly heat conductive material, etc. As an illustrative example, the mesh can be cooled in the step 920 by allowing at any temperature in the range of about 0° C. to about 23° C. for a period of time in the range of about 1 minute to about 20 minutes.

The temperature and amount of time at which the mesh is heated can provide additional rigidity or structural bias to the mesh, thereby at least partially enabling the resultant prosthesis to possess the characteristic of independently assuming and reassuming a predetermined three-dimensional shape. For example, steps 918 generally can include heating the mesh at or near its melting point, and subsequently cooling the mesh while in a three-dimensional shape.

One of skill in the art can appreciate that numerous of these steps can be removed or rearranged in order to manufacture different embodiments as described herein. For example, in embodiments where the prosthesis is not coated, steps 912 and 914 can be removed. Additionally, the mesh, coating, and template can be provided by external or internal means, e.g., by purchasing from a vendor or by manufacturing from one or more starting materials. Furthermore, the steps described in FIG. 9 can be performed by a single entity, person, group, business, etc., or by multiple entities, people, groups, business, etc., as would be appreciated by one of skill in the art.

Tests were performed on preformed, flexible coated prostheses that were manufactured according to the method of FIG. 9 and having any one of the shapes described herein with reference to FIGS. 1A through 3B. In particular, the resulting preformed coated prostheses were tested for suture retention strength, burst strength, elastic modulus, and pore size (i.e., the knit size) of the resulting mesh. The average suture retention strength was about 5.0 kgf, the average burst strength was about 67.8 kgf, and the average pore size was about 800 μm. One of skill in the art will appreciate that these values represent improved durability and further can provide tissue in-growth promotion for embodiments where in-growth is the desired fixation mechanism.

Notably, the edges of the thermoformed prosthesis need not be welded (e.g., using an ultrasonic welding process) and therefore need not form a perimeter having a different rigidity from an inner portion to maintain the preformed three-dimensional contoured shape. Additionally, it has been found that the value of about 140° C. for about 20 minutes represents a particularly illustrative value at which coating may be suitably heated without deteriorating the coating or resulting in it possessing undesirable properties, such as weakened suture retention strength, weakened burst strength, and an unsuitable value of elastic modulus. Alternatively, other temperatures such as 150° C. at lower periods of time can be used. Tests were performed on coated meshes that were heated at a temperature of about 150° C. for about 20 minutes. These tests demonstrated that a temperature of about 150° C. at about 20 minutes is not suitable for heating the coated mesh with the hydrolysable non-polymeric bioabsorbable cross-linked fatty acid based material. Specifically, when heated at about 150° C., the suture retention strength and the burst strength for the resulting prostheses were higher, due to pore size reduction caused by overheating. Additionally, the tests determined that silicon molds may be unsuitable, given that the silicon may strip away the coating during thermoforming.

The implantable prostheses described herein can be used to repair or prevent an existing or future defect in tissue or a muscle wall. For example, the prostheses can be used during totally extraperitoneal laparoscopic (TEP) inguinal hernia repairs. Such a prosthesis can be introduced to the treatment site via a posterior route, using a well known laparoscopy technique. Given that this technique is well known in the art, it will not be described in great detail herein. Generally, laparoscopic techniques include forming an extraperitoneal space between the fascia transversalis and the rectus and the transverse muscles, using any number of known techniques. For example, air can be supplied to create an air bubble that separates the peritoneum and the abdominal wall. Preferably, a balloon is inserted and inflated in order to create this space. One or more working trocars can be fitted in the space to enable the introduction of the prosthesis. Once implanted, the prosthesis can be positioned appropriately and sutured, if fixation by suturing is desired. Preferably, fixation occurs through tissue in-growth with the surrounding cells and biological environment.

As described herein, the particular three-dimensional contoured shape of the flexible, preformed prosthesis can be more adequately suited for accommodating the inguinal region in order to provide greater coverage of the repair site, easier deployment, and improved handling by surgeons. Furthermore, preformed coated prostheses according to embodiments of the present invention may be invertible so as to eliminate the need for separately manufacturing or purchasing right prostheses and left prostheses. The present invention includes embodiments able to independently assume a left orientation or a right orientation, and further being capable of inverting between the left and the right orientations. Additionally, preformed coated prostheses according to embodiments of the present invention can possess sufficiently uniform rigidity to enable trimming, cutting, altering, or otherwise removing/adapting portions of the body without reducing the prosthesis' ability to maintain the remaining subset of the predetermined three-dimensional contoured shape. This allows surgeons to more easily cut and customize prostheses prior to implantation based on a particular patient's body type, size, proportions, as well as based on the particular anatomical region containing the repair site and the specific characteristics of the anatomical defect.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. An implantable prosthesis for repairing a defect in a muscle or tissue wall, the prosthesis comprising:
   a seamless preformed flexible body having a three-dimensional contoured shape and comprising a first end, a second end opposite the first end, and a perimeter incorporating the first end and the second end;
   wherein the preformed flexible body independently assumes the contoured shape, the contoured shape comprising
      an open sided bowl at the first end of the preformed flexible body;
      a substantially planar area at the second end of the preformed flexible body; and
      a transitional area coupling the open sided bowl of the first end with the substantially planar area of the second end, the transitional area comprising an arch region coupled with a curved and banked region; and
   wherein, following along the perimeter, the arch region leads to the open sided bowl which leads to the curved and banked region which leads to the substantially planar area which leads to the arch region, thereby completing the perimeter, wherein rigidity of the preformed flexible body is substantially uniform throughout.

2. The prosthesis of claim 1, wherein the preformed flexible body is constructed from a single, continuous piece of material that has no rigidified perimeter imparting structure to form the contoured shape, and wherein the bowl lacks any sharp points.

3. The prosthesis of claim 1, wherein the preformed flexible body maintains a shape memory and thus is configured in such a way as to deform under at least a minimum predetermined force typically experienced during implantation against the muscle or tissue wall, and re-assume the contoured shape upon a release of the force.

4. The prosthesis of claim 1, wherein the substantially planar area is shaped and dimensioned to be affixed to a portion of a pelvic wall.

5. The prosthesis of claim 1, wherein the arch region is shaped and dimensioned to accommodate one or more external iliac vessels.

6. The prosthesis of claim 1, wherein the open sided bowl is shaped and dimensioned to substantially replicate the shape of a lateral extraperitoneal space.

7. The prosthesis of claim 1, wherein the curved and banked region is shaped and dimensioned to substantially replicate a shape of an abdominal wall.

8. The prosthesis of claim 1, wherein the preformed flexible body of the prosthesis is sized and dimensioned to cover a large direct hernia defect while being affixed to a Cooper's ligament.

9. The prosthesis of claim 1, wherein the perimeter is not rigidified relative to a remainder of the preformed flexible body.

10. The prosthesis of claim 1, wherein the perimeter has substantially the same rigidity as the preformed flexible body of the prosthesis.

11. The prosthesis of claim 1, wherein when an outer portion of the preformed flexible body is trimmed off, then the three-dimensional contoured shape of a remaining portion of the preformed flexible body does not substantially change.

12. The prosthesis of claim 1, wherein the preformed flexible body comprises a coated mesh that is preformed, the coated mesh including a non-polymeric bioabsorbable cross-linked fatty acid based material, the cross-links formed of ester bonds, lactone bonds, or both.

13. The prosthesis of claim 1, wherein the preformed flexible body further comprises a coating derived from eicosapentaenoic (EPA) and docosahexaenoic (DHA) fatty acids.

14. The prosthesis of claim 1, wherein the preformed flexible body further comprises a mesh having strands forming intersections, wherein a coating is at least partially disposed within the intersections.

15. The prosthesis of claim 1, wherein the preformed flexible body is invertible between a left orientation and a right orientation, the left orientation and the right orientation being substantially mirror images of each other.

16. The prosthesis of claim 1, wherein the preformed flexible body further comprises a mesh having strands forming a plurality of intersections, and wherein the three-dimensional contoured shape is maintained by interaction of the plurality of intersections with each other imparting structure to form and maintain the three-dimensional contoured shape.

17. An implantable prosthesis for repairing a defect in a muscle or tissue wall, the prosthesis comprising:
a preformed body configured to independently assume a predetermined three-dimensional contoured shape, the preformed body comprising
a single, seamless, and continuous piece of mesh having strands forming intersections;
a coating disposed at least partially within the intersections of the strands of the mesh; and
an inner portion and a perimeter surrounding the inner portion, wherein rigidity of the perimeter is substantially uniform.

18. The prosthesis of claim 17, wherein the three-dimensional contoured shape comprises:
an open sided bowl at a first end of the preformed body, wherein the bowl lacks any straight edges;
a substantially planar area at a second end of the preformed body opposite the first end; and
a transitional area coupling the open sided bowl of the first end with the substantially planar area of the second end, the transitional area comprising an arch region coupled with a curved and banked region;
wherein, following along the perimeter, the arch region leads to the open sided bowl which leads to the curved and banked region which leads to the substantially planar area which leads to the arch region, thereby completing the perimeter.

19. The prosthesis of claim 18, wherein the substantially planar area is shaped and dimensioned to be affixed to a portion of a pelvic wall.

20. The prosthesis of claim 18, wherein the arch region is shaped and dimensioned to accommodate one or more external iliac vessels.

21. The prosthesis of claim 18, wherein the open sided bowl is shaped and dimensioned to substantially replicate the shape of a lateral extraperitoneal space.

22. The prosthesis of claim 18, wherein the curved and banked region is shaped and dimensioned to substantially replicate a shape of an abdominal wall.

23. The prosthesis of claim 17, wherein the preformed body of the prosthesis is sized and dimensioned to cover a large direct hernia defect while being affixed to a Cooper's ligament.

24. The prosthesis of claim 17, wherein the preformed body is constructed from a single, continuous piece of material that has no rigidified perimeter imparting structure to form the contoured shape.

25. The prosthesis of claim 17, wherein the preformed body maintains a shape memory and thus is configured in such a way as to deform under at least a minimum predetermined force typically experienced during implantation against the muscle or tissue wall, and re-assume the contoured shape upon a release of the force.

26. The prosthesis of claim 17, wherein the perimeter is not rigidified relative to a remainder of the preformed body.

27. The prosthesis of claim 17, wherein a rigidity of the inner portion is substantially uniform.

28. The prosthesis of claim 17, wherein the perimeter has substantially the same rigidity as the preformed body of the prosthesis.

29. The prosthesis of claim 17, wherein when an outer portion of the preformed body is trimmed off, the three-dimensional contoured shape of a remaining portion of the preformed body does not substantially change.

30. The prosthesis of claim 17, wherein the preformed body comprises a coated mesh that is preformed, the coated mesh including a non-polymeric bioabsorbable cross-linked fatty acid based material, the cross-links formed of ester bonds, lactone bonds, or both.

31. The prosthesis of claim 17, wherein the preformed body is invertible between a left orientation and a right orientation, the left orientation and the right orientation being substantially mirror images of each other.

32. The prosthesis of claim 17, wherein the three-dimensional contoured shape is maintained by interaction of the intersections with each other imparting structure to form and maintain the three-dimensional contoured shape.

33. An implantable prosthesis for repairing a defect in a muscle or tissue wall, the prosthesis comprising:
a preformed flexible body comprising a single, continuous piece of preformed coated mesh, wherein the preformed flexible body is configured to independently assume a predetermined three-dimensional contoured shape that possesses no sharp point, the shape comprising
a substantially planar area; and
one or more non-uniform curvatures deviating away from the substantially planar area;
wherein the preformed flexible body is invertible between a left orientation and a right orientation, the left orientation and the right orientation being substantially mirror images of each other, and wherein the preformed coated mesh comprises coated strands forming a plurality of intersections, and wherein the three-dimensional contoured shape is maintained by interaction of the plurality of intersections with each other imparting structure to form and maintain the three-dimensional contoured shape.

34. The prosthesis of claim 33, further wherein the shape of the preformed flexible body comprises:
an open sided bowl at a first end of the preformed flexible body;
the substantially planar area at a second end of the preformed flexible body opposite the first end; and
a transitional area coupling the open sided bowl of the first end with the substantially planar area of the second end, the transitional area comprising an arch region coupled with a curved and banked region;
wherein, following along a perimeter, the arch region leads to the open sided bowl which leads to the curved and banked region which leads to the substantially planar area which leads to the arch region, thereby completing the perimeter.

35. The prosthesis of claim 34, wherein the arch region is shaped and dimensioned to accommodate one or more external iliac vessels.

36. The prosthesis of claim 34, wherein the curved and banked region is shaped and dimensioned to substantially replicate a shape of an abdominal wall.

37. The prosthesis of claim 34, wherein the open sided bowl is shaped and dimensioned to substantially replicate the shape of a lateral extraperitoneal space.

38. The prosthesis of claim 34, wherein the perimeter is not rigidified relative to a remainder of the preformed flexible body.

39. The prosthesis of claim 33, wherein the preformed flexible body maintains a shape memory and thus is configured in such a way as to deform under at least a minimum predetermined force typically experienced during implantation against the muscle or tissue wall, and re-assume the contoured shape upon a release of the force.

40. The prosthesis of claim 33, wherein the substantially planar area is shaped and dimensioned to be affixed to a portion of a pelvic wall.

41. The prosthesis of claim 33, wherein the preformed flexible body of the prosthesis is sized and dimensioned to cover a large direct hernia defect while being affixed to a Cooper's ligament.

42. The prosthesis of claim 33, wherein an entire perimeter has substantially the same rigidity as the preformed flexible body of the prosthesis.

43. The prosthesis of claim 33, wherein the shape comprises an outer portion extending along an entire perimeter and a remaining inner portion enclosed within the outer portion, wherein a rigidity of the inner portion is substantially uniform and further wherein a rigidity of the outer portion is substantially uniform, and further wherein the rigidity of the outer portion is substantially equal to the rigidity of the inner portion, such that the inner portion and the outer portion have substantially the same rigidity.

44. The prosthesis of claim 33, wherein when an outer portion of the preformed flexible body is trimmed off, the three-dimensional contoured shape of a remaining portion of the preformed flexible body does not substantially change.

45. The prosthesis of claim 33, wherein the coated mesh includes a non-polymeric bioabsorbable cross-linked fatty acid based material, the cross-links formed of ester bonds, lactone bonds, or both.

46. A method for fabricating an implantable prosthesis for repairing a defect in a muscle or tissue wall, the method comprising:
providing a coating to a single piece of mesh comprising strands forming a plurality of intersections, such that the coating is disposed at least partially within the intersections of the mesh;
curing the coating on the mesh at one or more predetermined temperatures for one or more predetermined times;
providing a template having a predetermined shape;
placing the mesh in the template;
heating the mesh in the template at one or more predetermined temperatures for one or more predetermined times so that the mesh retains the predetermined shape, thereby forming the implantable prosthesis; and
removing the implantable prosthesis from the template, wherein the implantable prosthesis comprises
a preformed flexible body comprising a single, continuous piece of preformed coated mesh, wherein the preformed flexible body is configured to independently assume a predetermined three-dimensional contoured shape that possesses no sharp point, the shape comprising
a substantially planar area; and
one or more non-uniform curvatures deviating away from the substantially planar area;
wherein the preformed flexible body is invertible between a left orientation and a right orientation, wherein the left orientation and the right orientation are substantially mirror images of each other, and wherein the preformed coated mesh comprises strands forming a plurality of intersections, and wherein the three-dimensional contoured shape is maintained by interaction of the plurality of intersections with each other imparting structure to form and maintain the three-dimensional contoured shape.

47. The method of claim 46, wherein the coating is provided by dipping, brushing, pumping, direct deposit via a conduit connected to a fluid reservoir.

48. The method of claim 46, wherein the mesh is heated at a temperature of about 130° C. to about 800° C. for a period of about 0.1 minutes to about 20 minutes.

49. The method of claim 46, wherein the coating on the mesh is cured at a temperature of about 50° C. to about 121° C. for a period of about 8 hours to about 48 hours.

50. The method of claim 46, further comprising cooling the mesh subsequent to heating the mesh.

51. The method of claim 46, further comprising cooling the mesh at a temperature of about 0° C. to about 23° C. for a period of about 1 minute to about 20 minutes.

52. The method of claim 46, further comprising subjecting the mesh to a force applied by a press while the mesh is being heated in the template.

53. The method of claim 46, wherein the predetermined shape of the prosthesis is maintained by interaction of the plurality of intersections with each other imparting structure to form and maintain the predetermined shape.

* * * * *